(12) United States Patent
Bengtsson et al.

(10) Patent No.: US 11,464,447 B2
(45) Date of Patent: Oct. 11, 2022

(54) REGIMEN ADHERENCE MEASURE FOR INSULIN TREATMENT BASED ON GLUCOSE MEASUREMENTS AND INSULIN PEN DATA

(71) Applicant: Novo Nordisk A/S, Bagsvaerd (DK)

(72) Inventors: Henrik Bengtsson, Taastrup (DK); Tinna Bjoerk Aradottir, Copenhagen (DK)

(73) Assignee: Novo Nordisk A/S, Bagsvaerd (DK)

( * ) Notice: Subject to any disclaimer, the term of this patent is extended or adjusted under 35 U.S.C. 154(b) by 313 days.

(21) Appl. No.: 16/307,098

(22) PCT Filed: Jun. 22, 2017

(86) PCT No.: PCT/EP2017/065379
§ 371 (c)(1),
(2) Date: Dec. 4, 2018

(87) PCT Pub. No.: WO2018/001853
PCT Pub. Date: Jan. 4, 2018

(65) Prior Publication Data
US 2020/0305788 A1    Oct. 1, 2020

(30) Foreign Application Priority Data

Jun. 30, 2016   (EP) .................................... 16177080

(51) Int. Cl.
*G16H 20/17* (2018.01)
*G16H 10/40* (2018.01)
(Continued)

(52) U.S. Cl.
CPC .......... *A61B 5/4833* (2013.01); *A61B 5/0004* (2013.01); *A61B 5/14532* (2013.01);
(Continued)

(58) Field of Classification Search
CPC . A61B 5/4833; A61B 5/0004; A61B 5/14532; A61B 5/4839; A61B 5/4866;
(Continued)

(56) References Cited

U.S. PATENT DOCUMENTS

| 7,752,058 B2 | 7/2010 | Sasaki et al. |
| 9,131,903 B2 | 9/2015 | Tokita et al. |

(Continued)

FOREIGN PATENT DOCUMENTS

| AU | 2015/100005 A4 | 2/2015 |
| JP | 2002169896 A | 6/2002 |

(Continued)

OTHER PUBLICATIONS

Fletcher, Lauren, et al. "Feasibility of an implanted, closed-loop, blood-glucose control device." Immunology 230. (Year: 2001).*

(Continued)

*Primary Examiner* — Patrick Fernandes
*Assistant Examiner* — Liam A Wallace
(74) *Attorney, Agent, or Firm* — Wesley Nicolas

(57) ABSTRACT

Systems and methods are provided for adjusting a standing insulin medicament dosage regimen for a subject. Fasting events are identified using autonomous timestamped glucose measurements of the subject in a first data set. A second data set, from one or more insulin pens used to apply the standing regimen, comprises records, each record comprising a time-stamped event specifying an amount of injected insulin medicament. Each fasting event is characterized as adherent or nonadherent. A fasting event is adherent when the second data set includes one or more records that temporally and quantitatively establish adherence with the standing regimen during the fasting event. Conversely, a fasting event is nonadherent when the second data set fails to temporally and quantitatively establish adherence with the standing regi-
(Continued)

men. Dosages in the standing regimen are adjusted using glucose measurements contemporaneous with adherent fasting events and by excluding glucose measurements contemporaneous with nonadherent fasting events.

15 Claims, 16 Drawing Sheets

(51) Int. Cl.
  G16H 20/60 (2018.01)
  A61B 5/00 (2006.01)
  A61B 5/145 (2006.01)
(52) U.S. Cl.
  CPC .......... *A61B 5/4839* (2013.01); *A61B 5/4866* (2013.01); *A61B 5/725* (2013.01); *G16H 10/40* (2018.01); *G16H 20/17* (2018.01); *G16H 20/60* (2018.01)
(58) Field of Classification Search
  CPC ........ A61B 5/725; G16H 20/17; G16H 20/60; G16H 10/40
  See application file for complete search history.

(56) References Cited

U.S. PATENT DOCUMENTS

| | | | |
|---|---|---|---|
| 9,597,019 B2 | 3/2017 | Ray et al. | |
| 9,619,625 B2 | 4/2017 | Bengtsson | |
| 9,737,665 B2 | 8/2017 | Heumann et al. | |
| 10,039,478 B2 | 8/2018 | Kasahara et al. | |
| 10,327,681 B2 | 6/2019 | Doyle, III et al. | |
| 2010/0057042 A1* | 3/2010 | Hayter | A61B 5/7275 604/504 |
| 2010/0331627 A1* | 12/2010 | Thukral | G16H 20/10 600/300 |
| 2011/0124996 A1 | 5/2011 | Reinke et al. | |
| 2013/0245545 A1 | 9/2013 | Arnold et al. | |
| 2013/0304389 A1* | 11/2013 | Li | A61B 5/7203 702/19 |
| 2014/0019396 A1* | 1/2014 | Carlsgaard | G06N 5/02 706/46 |
| 2014/0344280 A1 | 11/2014 | Wei et al. | |
| 2015/0006462 A1 | 1/2015 | Sudharsan | |
| 2016/0082187 A1 | 3/2016 | Schaible et al. | |
| 2016/0117481 A1* | 4/2016 | Booth | A61B 5/14503 604/502 |
| 2016/0132660 A1 | 5/2016 | Barajas et al. | |
| 2017/0132392 A1 | 5/2017 | Gerken | |
| 2017/0185748 A1* | 6/2017 | Budiman | A61B 5/7282 |

FOREIGN PATENT DOCUMENTS

| | | |
|---|---|---|
| JP | 2007267870 A | 10/2007 |
| JP | 2008197102 A | 8/2008 |
| JP | 2013188240 A | 9/2013 |
| JP | 2014514046 A | 6/2014 |
| JP | 2015142663 A | 8/2015 |
| JP | 2016515454 A | 5/2016 |
| JP | 2016531334 A | 10/2016 |
| JP | 2017501765 A | 1/2017 |
| JP | 2017524427 A | 8/2017 |
| JP | 2017532113 A | 11/2017 |
| KR | 20090095073 A | 9/2009 |
| WO | 2012152628 A1 | 11/2012 |
| WO | 2012153295 A2 | 11/2012 |
| WO | 2012156323 A1 | 11/2012 |
| WO | 2013022775 A1 | 2/2013 |
| WO | 2013032965 A1 | 3/2013 |
| WO | 2013146242 A1 | 10/2013 |
| WO | 2014037365 A1 | 3/2014 |
| WO | 2014197774 A2 | 12/2014 |
| WO | 2015073211 A1 | 5/2015 |
| WO | 2015197749 A1 | 12/2015 |
| WO | 2016048823 A1 | 3/2016 |

OTHER PUBLICATIONS

Abbott Freestyle Libre Flash Glucose Monitoring System "Abbott Diabetes Care," Abbott, 2015. [Online]. Available: https://abbottdiabetescare.co.uk/our-products/freestyle-libre. [Accessed Jul. 7, 2016]. 3 Pages.

Dassau, Bequette, Buckingham, Doyle. Detection of a Meal Using Continuous Glucose Monitoring. Emerging Treatments and Technologies. Diabetes Care 2008, vol. 31 No 2, pp. 295-300.

* cited by examiner

Methods for adjusting a standing insulin regimen 206 for a subject using a device 200 are provided. The standing insulin regimen comprises a basal insulin medicament dosage regimen 209. A first data set 220 is obtained. The first data set comprises a plurality of autonomous glucose measurements of the subject. Each respective autonomous glucose measurement 222 in the plurality of autonomous glucose measurements includes a timestamp 224 representing when the respective measurement was made. — 402, 404

Successive measurements in the plurality of autonomous glucose measurements are taken from the subject at an interval rate of 5 minutes or less, 3 minutes or less, or 1 minute or less.

A second data set 228 is obtained from one or more insulin pens used by the subject to apply the standing insulin regimen. The second data set comprises a plurality of insulin medicament records. Each insulin medicament record 230 in the plurality of medicament records comprises: (i) a respective insulin medicament injection event 232 including an amount of insulin medicament injected 234 into the subject using a respective insulin pen in the one or more insulin pens and (ii) a corresponding electronic timestamp 238 that is automatically generated by the respective insulin pen 104 upon occurrence of the respective insulin medicament injection event. — 406, 408

The device 200 further comprises a wireless receiver 284. The first data set is obtained wirelessly from a glucose sensor 102 affixed to the subject and/ or the second data set is obtained wirelessly from the one or more insulin pens using the wireless receiver.

Identify a plurality of fasting events using the plurality of autonomous glucose measurements of the subject and the respective timestamps in the first data set. — 410, 412

Identify a first fasting period (in the plurality of fasting events) in a first time period encompassed by the plurality of autonomous glucose measurements by (1) computing a moving period of variance $\sigma_k^2$ across the plurality of autonomous glucose measurements, where:

$$\sigma_k^2 = \left(\frac{1}{M}\sum_{i=k-M}^{k}(G_i - \bar{G})\right)^2$$

and where, $G_i$ is the $i^{th}$ glucose measurements in the portion k of the plurality of glucose measurements, M is a number of glucose measurements in the plurality of glucose measurements and represents a contiguous predetermined time span, $\bar{G}$ is the mean of the M glucose measurements selected from the plurality of glucose measurements, and k is within the first time period; and (2) associating the first fasting period with a period of minimum variance $\min_k \sigma_k^2$ within the first time period.

```
                                                                    ┌─ 414
┌─────────────────────────────────────────────────────────────────┐┘
│ Apply a first characterization 244 to each respective fasting event 242 in the
│ plurality of fasting events. The first characterization is one of basal regimen
│ adherent and basal regimen nonadherent. A respective fasting event is deemed
│ basal regimen adherent when the second data set includes one or more medicament
│ records that establish, on a temporal and quantitative basis, adherence with the
│ standing basal insulin medicament dosage regimen during the respective fasting
│ event. A respective fasting event is deemed basal regimen nonadherent when the
│ second data set fails to include one or more medicament records that establish, on
│ a temporal and quantitative basis, adherence with the standing basal insulin
│ medicament dosage regimen during the respective fasting event.         ┌─ 416
│  ┌ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─┘
│  │ The basal regimen specifies that a basal dose of long acting insulin      │
│  │ medicament 210 is to be taken during each respective epoch 212 in a       │
│  │ plurality of epochs and wherein a respective fasting event is deemed basal│
│  │ regimen nonadherent when there are no medicament records in the second    │
│  │ data set for the epoch associated with the respective fasting event.      │
│  │                                                                      ┌─ 418
│  │   ┌ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┐┘
│  │   │ Each epoch in the plurality of epochs is two days or less, one day or │ │
│  │   │ less, or 12 hours or less.                                            │ │
│  │   └ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┘
│  └ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─┘
└─────────────────────────────────────────────────────────────────┘
                                                                    ┌─ 420
┌─────────────────────────────────────────────────────────────────┐┘
│ Adjust amounts of insulin medicament dosage in the basal insulin medicament
│ dosage regimen for the subject based upon glucose measurements in the first
│ data set that are contemporaneous with the fasting events that are deemed basal
│ regimen adherent and by excluding glucose measurements in the first data set
│ that are contemporaneous with fasting events that are deemed basal regimen
│ nonadherent.
└─────────────────────────────────────────────────────────────────┘
```

The standing insulin regimen further comprises a bolus insulin medicament dosage regimen 214. Each respective insulin medicament injection event 232 in the plurality of medicament records further indicates a respective type of insulin medicament 236 injected into the subject from one of (i) a long acting insulin medicament and (ii) a short acting insulin medicament. The method further comprises:

identifying a plurality of meal events 246 using the plurality of autonomous glucose measurements and the corresponding timestamps in the first data set;

applying a second characterization 250 to each respective meal event 248 in the plurality of meal events, where the second characterization is one of bolus regimen adherent and bolus regimen nonadherent, a respective meal is deemed bolus regimen adherent when one or more medicament records in the plurality of medicament records indicates, on a temporal basis, a quantitative basis and a type of insulin medicament basis, adherence with the standing bolus insulin medicament dosage regimen during the respective meal, and a respective meal is deemed bolus regimen nonadherent when the plurality of medicament records fails to indicate adherence, on a temporal basis, a quantitative basis, and a type of insulin medicament basis, with the standing bolus insulin medicament dosage regimen during the respective meal; and adjusting insulin medicament dosage in the bolus insulin medicament dosage regimen for the subject by using glucose measurements in the first data set that are temporally associated with meal events that are deemed bolus regimen adherent and by excluding glucose measurements in the first data set that are temporally associated with meal events that are deemed bolus regimen nonadherent.

424

The first data set further comprises a plurality of feed-forward events, each respective feed-forward event 226 in the plurality of feed-forward events represents an instance where the subject has indicated they are having or are about to have a meal. The plurality of meal events are verified against the plurality of feed-forward events by either removing any respective meal event in the plurality of meal events that fails to temporally match any feed-forward event in the plurality of feed-forward events.

The bolus insulin medicament dosage regimen specifies that the short acting insulin medicament is to be taken up to a predetermined amount of time prior to a meal. A respective meal is deemed bolus regimen nonadherent when there is no insulin medicament record of the short acting insulin medicament type having an electronic timestamp up to the predetermined amount of time prior to the respective meal.

428

The predetermined amount of time is thirty minutes or less, twenty minutes or less, or fifteen minutes or less.

430

The long acting insulin medicament consists of a single insulin medicament having a duration of action that is between 12 and 24 hours or a mixture of insulin medicaments that collectively have a duration of action that is between 12 and 24 hours. The short acting insulin medicament consists of a single insulin medicament having a duration of action that is between three to eight hours or a mixture of insulin medicaments that collectively have a duration of action that is between three to eight hours.

432

The identifying the plurality of meal events is performed by computing:
    (i) a first model comprising a backward difference estimate of glucose rate of change using the plurality of autonomous glucose measurements,
    (ii) a second model comprising a backward difference estimate of glucose rate of change based on Kalman filtered estimates of glucose using the plurality of autonomous glucose measurements,
    (iii) a third model comprising a Kalman filtered estimate of glucose and Kalman filtered estimate of rate of change (ROC) of glucose based on the plurality of autonomous glucose measurements, and/or
    (iv) a fourth model comprising a Kalman filtered estimate of rate of change of ROC of glucose based on the plurality of autonomous glucose measurements.

434

The first model, the second model, the third model and the fourth model are each computed across the plurality of autonomous glucose measurements and each respective meal event in the plurality of meal events is identified at an instance where at least three of the four models indicates a meal event.

436

Repeat the method on an ongoing basis over time.

Fig. 4D

REGIMEN ADHERENCE MEASURE FOR INSULIN TREATMENT BASED ON GLUCOSE MEASUREMENTS AND INSULIN PEN DATA

CROSS-REFERENCE TO RELATED APPLICATIONS

This application is a 35 U.S.C. § 371 National Stage application of International Application PCT/EP2017/065379 (published as WO 2018/001853), filed Jun. 22, 2017, which claims priority to European Patent Application 16177080.5, filed Jun. 30, 2016, the contents of all above-named applications are incorporated herein by reference.

TECHNICAL FIELD

The present disclosure relates generally to systems and methods for assisting patients and health care practitioners in managing insulin delivery to diabetic patients.

BACKGROUND

Type 2 diabetes mellitus is characterized by progressive disruption of normal physiologic insulin secretion. In healthy individuals, basal insulin secretion by pancreatic β cells occurs continuously to maintain steady glucose levels for extended periods between meals. Also in healthy individuals, there is prandial secretion in which insulin is rapidly released in an initial first-phase spike in response to a meal, followed by prolonged insulin secretion that returns to basal levels after 2-3 hours.

Insulin is a hormone that binds to insulin receptors to lower blood glucose by facilitating cellular uptake of glucose, amino acids, and fatty acids into skeletal muscle and fat and by inhibiting the output of glucose from the liver. In normal healthy individuals, physiologic basal and prandial insulin secretions maintain euglycemia, which affects fasting plasma glucose and postprandial plasma glucose concentrations. Basal and prandial insulin secretion is impaired in Type 2 diabetes and early post-meal response is absent. To address these adverse events, patients with Type 2 diabetes are provided with insulin treatment regimens. Patients with Type 1 diabetes are also provided with insulin treatment regimens.

Some diabetic patients only need a basal insulin treatment regimen to make up for deficiencies in pancreatic β cells insulin secretion. Some patients need both basal insulin treatment and bolus insulin treatment. Thus, patients that require both basal insulin treatment and bolus insulin treatment take a periodic basal insulin medicament treatment, for instance once or twice a day, as well as one or more bolus insulin medicament treatments with meals.

The goal of these insulin treatment regimens is to achieve steady glucose levels. The success of an insulin treatment regimen in a subject can be deduced by taking continuous glucose level measurements of a subject or by measuring HbA1c levels. The term "HbA1c" refers to glycated haemoglobin. It develops when haemoglobin, a protein within red blood cells that carries oxygen throughout the body, joins with glucose in the blood, thus becoming "glycated." By measuring glycated haemoglobin (HbA1c), health care practitioners are able to get an overall picture of average glucose levels over a period of weeks/months. For people with diabetes, the higher the HbA1c, the greater the risk of developing diabetes-related complications Insulin treatment regimen nonadherence is a barrier for diabetes patients to reaching suitable HbA1c goals. Adherence is typically defined as the degree to which a patient correctly follows medical advice (e.g., a standing insulin regimen for a subject comprising at least a basal insulin medicament dosage regimen), but can also be, for example, consistency in diet and exercise. The reasons for nonadherence are many and different. One reason for nonadherence is poor health literacy and comprehension of treatment. Patients fail to understand glucose measurement results, lack positive feedback when adherent, or feel a lack of urgency. Another reason for nonadherence is the fear of side effects. For instance, the fear of hypoglycaemia if the patient strictly adheres to the standing insulin regimen. Yet another reason for nonadherence is the hassle and time-consuming aspect of conventional standing insulin regimens, which often entail home-logging data and frequent injections and glucose measurements.

Patients on insulin pen treatment typically use blood glucose monitors, and need to home-log measurements and injections in order to adhere to standing insulin regimens. These home-logged data tend to be unreliable due to several reasons. In some instances, patients hide regimen nonadherence by filling in better (lower) blood glucose measurements than observed or non-taken insulin injections as taken. In some instances, patients do not regularly fill out log-books and therefore do so by memory the evening before a meeting with a health care practitioner.

As such, health care practitioners are forced to navigate with home-logged data which poses difficulty in pinpointing where and why treatment is going wrong. Moreover, the unreliability of home-logged data can lead to adverse events. For instance, the heath care practitioner may up-titrate a basal insulin medicament when the patient exhibits fasting blood glucose measurements that are too high. Yet, this may lead to the adverse event of overdosing of the insulin medicament and hypoglycemia when the blood glucose measurements were in fact due to forgotten basal or bolus insulin medicament injections, as opposed to an insulin regimen that did not call for adequate insulin medicament dosing. Also, the patient may log as non-taken insulin medicament doses as taken. When this is not reflected in glucose levels measured in the clinic (and/or HbA1c levels measured from such glucose levels), the health care practitioner may increase insulin medicament dosage in the standing insulin regimen for this basis and thus the patient's dosage regimen can therefore indicate a dangerously high insulin dose, if injected, leading to overdosing of the insulin medicament and hypoglycemia.

Given the inadequacy with patient recorded records disclosed above, what is needed in the art are systems and methods that provide more robust insulin titration methods that achieve target glucose levels.

SUMMARY

In the disclosure of the present invention, embodiments and aspects will be described, which will address one or more of the above objects or which will 6address objects apparent from the below disclosure as well as from the description of exemplary embodiments.

The present disclosure addresses the above-identified need in the art by providing a patient and/or health care practitioner with ways to monitor adherence with a standing insulin regimen and to thereby enable the pinpointing how adherence, and to what degree, regimen adherence affects the treatment results for the patient. As such, the present disclosure relates to analyzing autonomous glucose measurements and insulin pen data of a patient, and potentially more data, such as from wearables, to assist health care practitioners and/or the patient in obtaining treatment transparency.

In one aspect of the present disclosure, systems and methods are provided for adjusting a standing insulin medicament dosage regimen for a subject. Fasting events are identified using autonomous timestamped glucose measurements of the subject in a first data set. Further, a second data set is obtained from one or more insulin pens used to apply the standing regimen to the subject. This second data set comprises records. Each record comprises a timestamped event specifying an amount of injected insulin medicament that the subject injected as part of the standing insulin medicament dosage regimen. Each fasting event is characterized as adherent or nonadherent. A fasting event is adherent when the second data set includes one or more records that temporally and quantitatively establish adherence with the standing regimen during the fasting event. Conversely, a fasting event is nonadherent when the second data set fails to temporally and quantitatively establish adherence with the standing regimen. Dosages in the standing regimen are adjusted using glucose measurements contemporaneous with adherent fasting events and by specifically excluding glucose measurements contemporaneous with nonadherent fasting events. This helps to overcome inaccuracies that arise in conventional home-logged insulin treatment data.

In a further aspect the standing insulin regimen comprises a bolus insulin medicament dosage regimen, each respective insulin medicament injection event in the plurality of medicament records further indicates a respective type of insulin medicament injected into the subject from one of (i) a long acting insulin medicament and (ii) a short acting insulin medicament, and the method further comprises: identifying a plurality of meal events using the plurality of autonomous glucose measurements and the corresponding timestamps in the first data set, and applying a second characterization to each respective meal event in the plurality of meal events. The second characterization is one of a bolus regimen adherent and a bolus regimen nonadherent, a respective meal is deemed bolus regimen adherent when one or more medicament records in the plurality of medicament records indicates, on a temporal basis, a quantitative basis and a type of insulin medicament basis, adherence with the standing bolus insulin medicament dosage regimen during the respective meal. A respective meal is deemed bolus regimen nonadherent when the plurality of medicament records fails to indicate adherence, on a temporal basis, a quantitative basis, and a type of insulin medicament basis, with the standing bolus insulin medicament dosage regimen during the respective meal. The method further comprises adjusting insulin medicament dosage in the standing insulin medicament regimen for the subject by using glucose measurements in the first data set that are temporally associated with meal events that are deemed bolus regimen adherent and by excluding glucose measurements in the first data set that are temporally associated with meal events that are deemed bolus regimen nonadherent.

In a further aspect the method comprises adjusting insulin medicament dosage in the bolus insulin medicament dosage regimen for the subject by using glucose measurements in the first data set that are temporally associated with meal events that are deemed bolus regimen adherent and by excluding glucose measurements in the first data set that are temporally associated with meal events that are deemed bolus regimen nonadherent.

In a further aspect the method comprises adjusting insulin medicament dosage in the basal insulin medicament dosage regimen for the subject by using glucose measurements in the first data set that are temporally associated with meal events that are deemed bolus regimen adherent and by excluding glucose measurements in the first data set that are temporally associated with meal events that are deemed bolus regimen nonadherent.

In a further aspect, the device further comprising a wireless receiver, and wherein the first data set is obtained wirelessly from a glucose sensor affixed to the subject and/or the second data set is obtained wirelessly from the one or more insulin pens.

In a further aspect, the first data set further comprises a plurality of feed-forward events, each respective feed-forward event in the plurality of feed-forward events represents an instance where the subject has indicated they are having or are about to have a meal, and the plurality of meal events are verified against the plurality of feed-forward events by either removing any respective meal event in the plurality of meal events that fails to temporally match any feed-forward event in the plurality of feed-forward events.

In a further aspect successive measurements in the plurality of autonomous glucose measurements are taken from the subject at an interval rate of 5 minutes or less, 3 minutes or less, or 1 minute or less.

In a further aspect the basal regimen is associated with a plurality of epochs, the basal regimen specifies that a basal dose of long acting insulin medicament is to be taken during each respective epoch in the plurality of epochs, and a respective fasting event is deemed basal regimen nonadherent, when there are no medicament records in the second data set for the epoch associated with the respective fasting event.

In a further aspect each epoch in the plurality of epochs is one week or less, two days or less, one day or less, or 12 hours or less.

In a further aspect, the bolus insulin medicament dosage regimen specifies that the short acting insulin medicament is to be taken up to a predetermined amount of time prior to or after a meal, and a respective meal is deemed bolus regimen nonadherent when there is no insulin medicament record of the short acting insulin medicament type having an electronic timestamp up to the predetermined amount of time prior to or after the respective meal.

In a further aspect, the predetermined amount of time is thirty minutes or less, twenty minutes or less, or fifteen minutes or less.

In a further aspect, the long acting insulin medicament consists of a single insulin medicament having a duration of action that is between 12 and 24 hours or a mixture of insulin medicaments that collectively have a duration of action that is between 12 and 24 hours, and the short acting insulin medicament consists of a single insulin medicament having a duration of action that is between three to eight hours or a mixture of insulin medicaments that collectively have a duration of action that is between three to eight hours.

In a an other aspect, the long acting insulin medicament consists of a single insulin medicament having a duration of action that is between 24 hours and one a week.

In a further aspect the identifying the plurality of meal events is performed by computing:
(i) a first model comprising a backward difference estimate of glucose rate of change using the plurality of autonomous glucose measurements,
(ii) a second model comprising a backward difference estimate of glucose rate of change based on Kalman filtered estimates of glucose using the plurality of autonomous glucose measurements, (iii) a third model comprising a Kalman filtered estimate of glucose and Kalman filtered estimate of rate of change (ROC) of glucose based on the plurality of autonomous glucose measurements, or (iv) a fourth model comprising a Kalman filtered estimate of rate of change of ROC of glucose based on the plurality of autonomous glucose measurements.

In a further aspect, the first model, the second model, the third model and the fourth model are each computed across the plurality of autonomous glucose measurements and each respective meal event in the plurality of meal events is identified at an instance where at least three of the four models indicates a meal event.

In a further aspect, the method further comprises repeating the method on an ongoing basis over time.

In a further aspect, the identifying the plurality of fasting events comprises identifying a first fasting period in a first time period encompassed by the plurality of autonomous glucose measurements by:

computing a moving period of variance $\sigma_k^2$ across the plurality of autonomous glucose measurements, wherein:

$$\sigma_k^2 = \left( \frac{1}{M} \sum_{i=k-M}^{k} (G_i - \bar{G}) \right)^2$$

wherein, $G_i$ is the $i^{th}$ autonomous glucose measurement in a portion k of the plurality of autonomous glucose measurements, M is a number of autonomous glucose measurements in the plurality of glucose measurements and represents a contiguous predetermined time span, $\bar{G}$ is the mean of the autonomous glucose measurements selected from the plurality of autonomous glucose measurements, and k is within the first time period; and associating the first fasting period with a period of minimum variance $$\min_k \sigma_k^2$$

within the first time period.

In another aspect of the present disclosure, a computer program is provided comprising instructions that, when executed by one or more processors, perform a method comprising:

obtaining a first data set, the first data set comprising a plurality of autonomous glucose measurements of the subject and, for each respective autonomous glucose measurement in the plurality of autonomous glucose measurements, a timestamp representing when the respective measurement was made;

obtaining a second data set from one or more insulin pens used by the subject to apply the standing insulin regimen, the second data set comprising a plurality of insulin medicament records, each insulin medicament record in the plurality of medicament records comprising: (i) a respective insulin medicament injection event including an amount of insulin medicament injected into the subject using a respective insulin pen in the one or more insulin pens and (ii) a corresponding electronic timestamp that is automatically generated by the respective insulin pen upon occurrence of the respective insulin medicament injection event;

identifying a plurality of fasting events using the plurality of autonomous glucose measurements of the subject and the respective timestamps in the first data set;

applying a first characterization to each respective fasting event in the plurality of fasting events, wherein
the first characterization is one of basal regimen adherent and basal regimen nonadherent,
a respective fasting event is deemed basal regimen adherent when the second data set includes one or more medicament records that establish, on a temporal and quantitative basis, adherence with the standing basal insulin medicament dosage regimen during the respective fasting event, and
a respective fasting event is deemed basal regimen nonadherent when the second data set fails to include one or more medicament records that establish, on a temporal and quantitative basis, adherence with the standing basal insulin medicament dosage regimen during the respective fasting event; and adjusting insulin medicament dosage in the basal insulin medicament dosage regimen for the subject based upon glucose measurements in the first data set that are contemporaneous with the fasting events that are deemed basal regimen adherent and by excluding glucose measurements in the first data set that are contemporaneous with fasting events that are deemed basal regimen nonadherent.

In a further aspect is provided a computer-readable data carrier having stored thereon the computer program.

BRIEF DESCRIPTION OF THE DRAWINGS

FIGS. 4A, 4B, 4C, and 4D collectively provide a flow chart of processes and features of a device for adjusting a standing insulin regimen for a subject in accordance with various embodiments of the present disclosure.

Like reference numerals refer to corresponding parts throughout the several views of the drawings.

DETAILED DESCRIPTION

Figure 5:
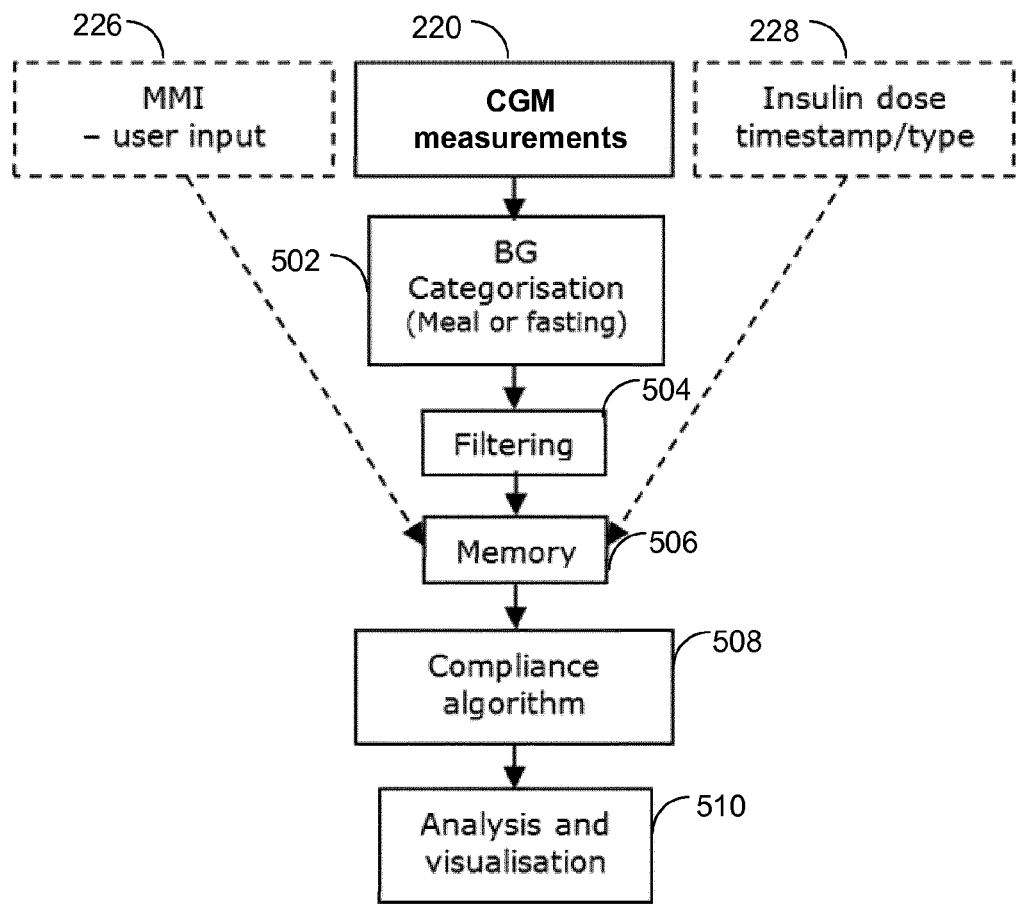
FIG. 5 illustrates an example integrated system of connected insulin pen, continuous glucose monitor, memory and a processor for performing algorithmic categorization of autonomous glucose data in accordance with an embodiment of the present disclosure.

FIG. 5 illustrates an example of an integrated system of one or more connected insulin pens, one or more continuous glucose monitors, memory and a processor for performing algorithmic categorization of autonomous glucose data of a subject in accordance with an embodiment of the present disclosure. Autonomous timestamped glucose measurements of the subject are obtained in a first data set 220. A second data set 228 is obtained from one or more insulin pens used to apply the standing regimen to the subject. This second data set comprises records. Each record comprises a timestamped event specifying an amount of injected insulin medicament that the subject injected as part of the standing insulin medicament dosage regimen. Fasting events are identified using autonomous timestamped glucose measurements of the subject in a first data set 502. Optionally meal events are also identified using the autonomous timestamped glucose measurements 502. In this way, the glucose measurements are filtered 504 and stored in memory 506. Each fasting event is characterized as adherent or nonadherent 508. A fasting event is adherent when the second data set includes one or more records that temporally and quantitatively establish adherence with a standing regimen during the fasting event. Conversely, a fasting event is nonadherent when the second data set fails to temporally and quantitatively establish adherence with the standing regimen. A respective meal is deemed bolus regimen adherent when one or more medicament records in the plurality of medicament records indicates, on a temporal basis, a quantitative basis and a type of insulin medicament basis, adherence with the standing bolus insulin medicament dosage regimen during the respective meal. A respective meal is deemed bolus regimen nonadherent when the plurality of medicament records fails to indicate adherence, on a temporal basis, a quantitative basis, and a type of insulin medicament basis, with the standing bolus insulin medicament dosage regimen during the respective meal. Finally, the filtered and cataloged glucose data is analyzed and visualized 510. Such visualization enables dosages in the standing regimen to be adjusted using glucose measurements contemporaneous with adherent fasting events and by specifically excluding glucose measurements contemporaneous with nonadherent fasting events. This helps to overcome inaccuracies that arise in conventional home-logged insulin treatment data.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject. Furthermore, the terms "subject" and "user" are used interchangeably herein. By the term insulin pen is meant an injection device suitable for applying discrete doses of insulin, and wherein the injection device is adapted for logging and communicating dose related data.

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

Figure 1:
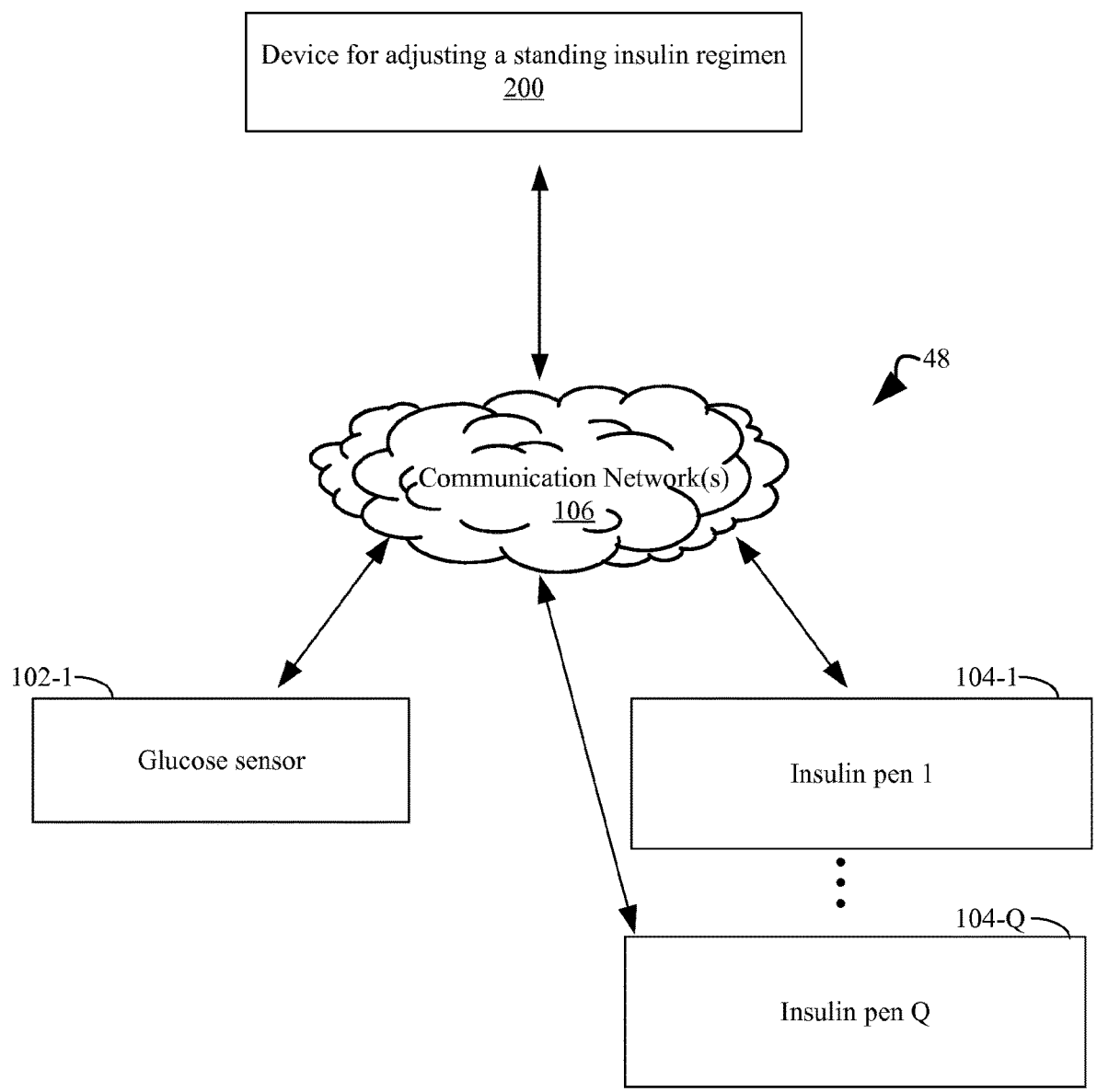
FIG. 1 illustrates an exemplary system topology that includes a device for adjusting a standing insulin regimen for a subject, one or more glucose sensors that autonomously measure glucose data from the subject, and one or more insulin pens that are used by the subject to inject insulin medicaments in accordance with a standing insulin regimen, where the one or more glucose sensors, the one or more insulin pens, and the device are interconnected, optionally through a communications network, in accordance with an embodiment of the present disclosure.
Figure 2:
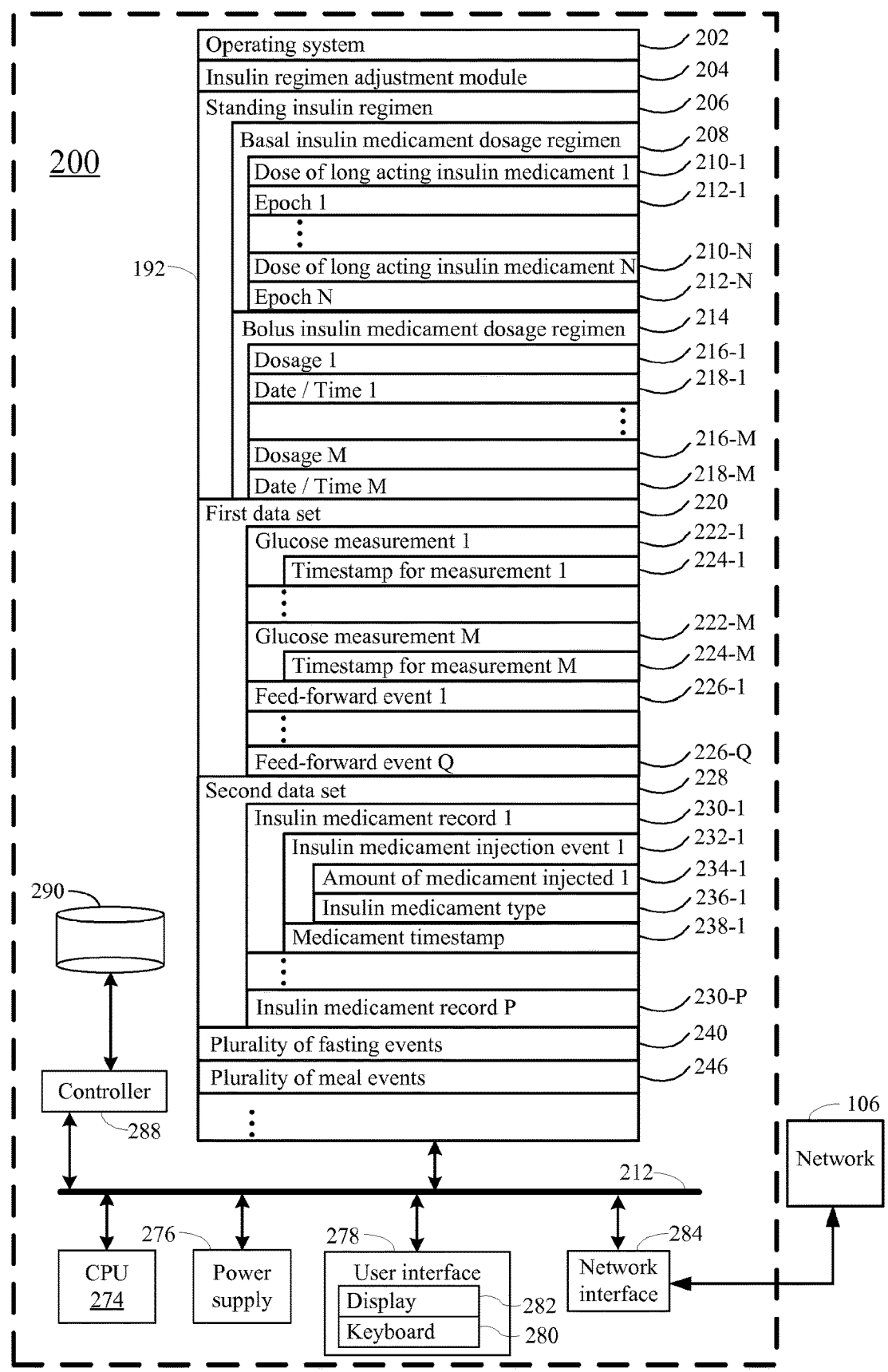
FIG. 2 illustrates a device for adjusting a standing insulin regimen for a subject in accordance with an embodiment of the present disclosure.
Figure 3:
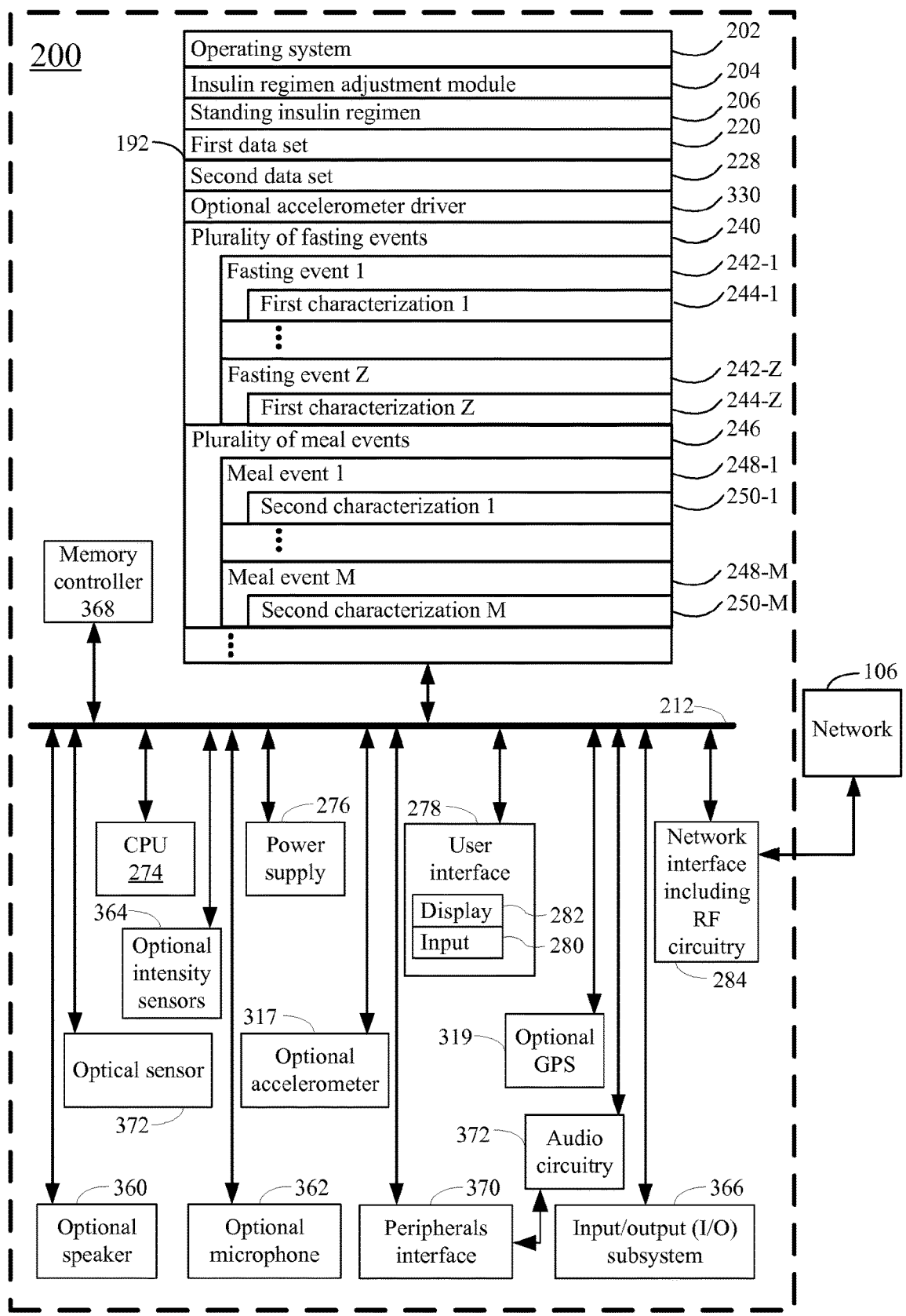
FIG. 3 illustrates a device for adjusting a standing insulin regimen for a subject in accordance with another embodiment of the present disclosure.

A detailed description of a system 48 for adjusting a standing insulin regimen 206 for a subject in accordance with the present disclosure is described in conjunction with FIGS. 1 through 3. As such, FIGS. 1 through 3 collectively illustrate the topology of the system in accordance with the present disclosure. In the topology, there is a device for adjusting a standing insulin regimen 200 for a subject (FIGS. 1, 2, and 2), one or more glucose sensors associated with the subject (FIG. 1), and one or more insulin pens for injecting insulin medicaments into the subject (FIG. 1).

Referring to FIG. 1, there is device 200 for adjusting a standing insulin regimen of a subject. To do this, the device 200 receives autonomous glucose measurements from a glucose sensor 102 attached to the subject on an ongoing basis. Further, the device 200 receives insulin medicament injection data from one or more insulin pens used by the subject to inject insulin medicaments. As disclosed herein in further detail, in some embodiments the device 200 receives this data wirelessly through radio-frequency signals. In some embodiments such signals are in accordance with an 802.11, Bluetooth, or ZigBee standard. In some embodiments, the device 200 is not proximate to the subject and/or does not have wireless capabilities or such wireless capabilities are not used for the purpose of acquiring glucose data and insulin medicament injection data. In such embodiments a communication network 106 may be used to communicate glucose measurements from the glucose sensor 102 to the device 200 and from the insulin pens 104 to the device 200.

Examples of networks 106 include, but are not limited to, the World Wide Web (WWW), an intranet and/or a wireless network, such as a cellular telephone network, a wireless local area network (LAN) and/or a metropolitan area network (MAN), and other devices by wireless communication. The wireless communication optionally uses any of a plurality of communications standards, protocols and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11ac, IEEE 802.11ax, IEEE 802.11b, IEEE 802.11g and/or IEEE 802.11n), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

In some embodiments the device 200 is part of the glucose sensor 102. That is, in some embodiments, the device 200 and the glucose sensor 102 are a single device.

In some embodiments the device 200 is part of the insulin pen. That is, in some embodiments, the device 200 and an insulin pen 104 are a single device.

Of course, other topologies of system 48 are possible. For instance, rather than relying on a communications network 106, the glucose sensor 102 and insulin pens may wirelessly transmit information directly to the device 200. Further, device 200 may constitute a portable electronic device, a server computer, or in fact constitute several computers that are linked together in a network or be a virtual machine in a cloud computing context. As such, the exemplary topology shown in FIG. 1 merely serves to describe the features of an embodiment of the present disclosure in a manner that will be readily understood to one of skill in the art.

Referring to FIG. 2, in typical embodiments, the device for adjusting a standing insulin regimen 200 comprises one or more computers. For purposes of illustration in FIG. 2, the device 200 is represented as a single computer that includes all of the functionality for adjusting a standing insulin regimen. However, the disclosure is not so limited. The functionality for adjusting a standing insulin regimen may be spread across any number of networked computers and/or reside on each of several networked computers and/or by hosted on one or more virtual machines at a remote location accessible across the communications network 106. One of skill in the art will appreciate that a wide array of different computer topologies are possible for the application and all such topologies are within the scope of the present disclosure.

Turning to FIG. 2 with the foregoing in mind, an exemplary device for adjusting a standing insulin regimen comprises one or more processing units (CPU's) 274, a network or other communications interface 284, a memory 192 (e.g., random access memory), one or more magnetic disk storage and/or persistent devices 290 optionally accessed by one or more controllers 288, one or more communication busses 212 for interconnecting the aforementioned components, and a power supply 276 for powering the aforementioned components. Data in memory 192 can be seamlessly shared with non-volatile memory 290 using known computing techniques such as caching. Memory 192 and/or memory 290 can include mass storage that is remotely located with respect to the central processing unit(s) 274. In other words, some data stored in memory 192 and/or memory 290 may in fact be hosted on computers that are external to the device 200 but that can be electronically accessed by the device 200 over an Internet, intranet, or other form of network or electronic cable (illustrated as element 106 in FIG. 2) using network interface 284.

The memory 192 of the device 200 for adjusting a standing insulin regimen 206 for a subject stores:
- an operating system 202 that includes procedures for handling various basic system services;
- an insulin regimen adjustment module 204;
- a standing insulin regimen 206 for a subject, the standing insulin regimen comprising a basal insulin medicament dosage regimen 208 and, optionally in some embodiments, a bolus insulin medicament dosage regimen 214;
- a first data set 220, the first data set comprising a plurality of autonomous glucose measurements of the subject and, for each respective autonomous glucose measurement 222 in the plurality of autonomous glucose measurements, a timestamp 224 representing when the respective measurement was made, as well as optionally, a plurality of feed-forward events 226;
- a second data set 228 comprising a plurality of insulin medicament records for a subject, each insulin medicament record 230 in the plurality of medicament records comprising: (i) a respective insulin medicament injection event 232 including an amount of insulin medicament injected 234 into the subject using a respective insulin pen in one or more insulin pens (ii) a corresponding electronic timestamp 238 that is automatically generated by a respective insulin pen 104 upon occurrence of the respective insulin medicament injection event, and optionally an insulin medicament type 236;

a plurality of fasting events 240 determined for the subject; and a plurality of meal events 246 determined for the subject.

In some embodiments, the insulin regimen adjustment module 204 is accessible within any browser (phone, tablet, laptop/desktop). In some embodiments the insulin regimen adjustment module 204 runs on native device frameworks, and is available for download onto the device 200 running an operating system 202 such as Android or iOS.

In some implementations, one or more of the above identified data elements or modules of the device 200 for adjusting a standing insulin regimen of a subject 206 are stored in one or more of the previously described memory devices, and correspond to a set of instructions for performing a function described above. The above-identified data, modules or programs (e.g., sets of instructions) need not be implemented as separate software programs, procedures or modules, and thus various subsets of these modules may be combined or otherwise re-arranged in various implementations. In some implementations, the memory 192 and/or 290 optionally stores a subset of the modules and data structures identified above. Furthermore, in some embodiments the memory 192 and/or 290 stores additional modules and data structures not described above.

In some embodiments, a device 200 for adjusting a standing insulin regimen 206 for a subject is a smart phone (e.g., an iPHONE), laptop, tablet computer, desktop computer, or other form of electronic device (e.g., a gaming console). In some embodiments, the device 200 is not mobile. In some embodiments, the device 200 is mobile.

FIG. 3 provides a further description of a device 200 that can be used with the instant disclosure. The device 200 illustrated in FIG. 3 has one or more processing units (CPU's) 274, peripherals interface 370, memory controller 368, a network or other communications interface 284, a memory 192 (e.g., random access memory), a user interface 278, the user interface 278 including a display 282 and input 280 (e.g., keyboard, keypad, touch screen), an optional accelerometer 317, an optional GPS 319, optional audio circuitry 372, an optional speaker 360, an optional microphone 362, one or more optional intensity sensors 364 for detecting intensity of contacts on the device 200 (e.g., a touch-sensitive surface such as a touch-sensitive display system 282 of the device 200), an optional input/output (I/O) subsystem 366, one or more optional optical sensors 372, one or more communication busses 212 for interconnecting the aforementioned components, and a power system 276 for powering the aforementioned components.

In some embodiments, the input 280 is a touch-sensitive display, such as a touch-sensitive surface. In some embodiments, the user interface 278 includes one or more soft keyboard embodiments. The soft keyboard embodiments may include standard (QWERTY) and/or non-standard configurations of symbols on the displayed icons.

The device 200 illustrated in FIG. 3 optionally includes, in addition to accelerometer(s) 317, a magnetometer (not shown) and a GPS 319 (or GLONASS or other global navigation system) receiver for obtaining information concerning the location and orientation (e.g., portrait or landscape) of the device 200 and/or for determining an amount of physical exertion by the subject.

It should be appreciated that the device 200 illustrated in FIG. 3 is only one example of a multifunction device that may be used for adjusting a standing insulin regimen 206 for a subject, and that the device 200 optionally has more or fewer components than shown, optionally combines two or more components, or optionally has a different configuration or arrangement of the components. The various components shown in FIG. 3 are implemented in hardware, software, firmware, or a combination thereof, including one or more signal processing and/or application specific integrated circuits.

Memory 192 of the device 200 illustrated in FIG. 3 optionally includes high-speed random access memory and optionally also includes non-volatile memory, such as one or more magnetic disk storage devices, flash memory devices, or other non-volatile solid-state memory devices. Access to memory 192 by other components of the device 200, such as CPU(s) 274 is, optionally, controlled by the memory controller 368.

The peripherals interface 370 can be used to couple input and output peripherals of the device to CPU(s) 274 and memory 192. The one or more processors 274 run or execute various software programs and/or sets of instructions stored in memory 192, such as the insulin regimen adjustment module 204, to perform various functions for the device 200 and to process data.

In some embodiments, the peripherals interface 370, CPU(s) 274, and memory controller 368 are, optionally, implemented on a single chip. In some other embodiments, they are, optionally, implemented on separate chips.

RF (radio frequency) circuitry of network interface 284 receives and sends RF signals, also called electromagnetic signals. In some embodiments, the plurality of glucose measurements 222 are received using this RF circuitry from a glucose sensor 102 associated with a subject. In some embodiments insulin medicament records 230 are received using this RF circuitry from one or more insulin pens 104 that subject uses to inject insulin medicaments. In some embodiments, RF circuitry 108 converts electrical signals to/from electromagnetic signals and communicates with communications networks and other communications devices, glucose sensors 102, and insulin pens 104 via the electromagnetic signals. RF circuitry 284 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 284 optionally communicates with the communication network 106. In some embodiments, the circuitry 284 does not include RF circuitry and, in fact, is connected to the network 106 through one or more hard wires (e.g., an optical cable, a coaxial cable, or the like).

In some embodiments, audio circuitry 372, optional speaker 360, and optional microphone 362 provide an audio interface between the subject and the device 200. The audio circuitry 372 receives audio data from peripherals interface 370, converts the audio data to electrical signals, and transmits the electrical signals to speaker 360. Speaker 360 converts the electrical signals to human-audible sound waves. Audio circuitry 372 also receives electrical signals converted by the microphone 362 from sound waves. Audio circuitry 372 converts the electrical signal to audio data and transmits the audio data to peripherals interface 370 for processing. Audio data is, optionally, retrieved from and/or transmitted to memory 192 and/or RF circuitry 284 by peripherals interface 370.

In some embodiments, the power supply 276 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

In some embodiments, the device 200 optionally also includes one or more optical sensors 372. The optical sensor(s) 372 optionally include charge-coupled device (CCD) or complementary metal-oxide semiconductor (CMOS) phototransistors. The optical sensor(s) 372 receive light from the environment, projected through one or more lens, and converts the light to data representing an image. The optical sensor(s) 372 optionally capture still images and/or video. In some embodiments, an optical sensor is located on the back of device 200, opposite the display 282 on the front of the device, so that the input 280 is enabled for use as a viewfinder for still and/or video image acquisition. In some embodiments, another optical sensor 372 is located on the front of the device 200 so that the subject's image is obtained (e.g., to verify the health or condition of the subject, to determine the physical activity level of the subject, or to help diagnose a subject's condition remotely, etc.).

As illustrated in FIG. 3, a device 200 preferably comprises an operating system 202 that includes procedures for handling various basic system services. Operating system 202 (e.g., iOS, DARWIN, RTXC, LINUX, UNIX, OS X, WINDOWS, or an embedded operating system such as VxWorks) includes various software components and/or drivers for controlling and managing general system tasks (e.g., memory management, storage device control, power management, etc.) and facilitates communication between various hardware and software components.

In some embodiments a device 200 is a smart phone. In other embodiments, a device 200 is not a smart phone but rather is a tablet computer, desktop computer, emergency vehicle computer, or other form or wired or wireless networked device. In some embodiments, the device 200 has any or all of the circuitry, hardware components, and software components found in the device 200 depicted in FIG. 2 or 3. In the interest of brevity and clarity, only a few of the possible components of the device 200 are shown in order to better emphasize the additional software modules that are installed on the device 200.

While the system 48 disclosed in FIG. 1 can work standalone, in some embodiments it can also be linked with electronic medical records to exchange information in any way.

Now that details of a system 48 for adjusting a standing insulin regimen (206) for a subject has been disclosed, details regarding a flow chart of processes and features of the system, in accordance with an embodiment of the present disclosure, are disclosed with reference to FIGS. 4A through 4D. In some embodiments, such processes and features of the system are carried out by the insulin regimen adjustment module 204 illustrated in FIGS. 2 and 3.

Block 402. The goal of insulin therapy in subjects with either type 1 diabetes mellitus or type 2 diabetes mellitus is to match as closely as possible normal physiologic insulin secretion to control fasting and postprandial plasma glucose. This is done with a standing insulin regimen 206 for the subject. One aspect of the present disclosure provides a device 200 for adjusting the standing insulin regimen. In the present disclosure, the standing insulin regimen comprises a basal insulin medicament dosage regimen 208. The device comprises one or more processors 274 and a memory 192/290. The memory stores instructions that, when executed by the one or more processors, perform a method. In the method, a first data set 220 is obtained.

The first data set comprises a plurality of autonomous glucose measurements of the subject from a glucose sensor 102. Each respective autonomous glucose measurement 222 in the plurality of autonomous glucose measurements includes a timestamp 224 representing when the respective measurement was made. The first data set may be in any format, and in fact may be spread across multiple files or data structures, provided that such files or data structures are addressable by the insulin regimen adjustment module 204 or equivalent process.

The FREESTYLE LIBRE CGM by ABBOTT ("LIBRE") is an example of a glucose sensor that may be used as a glucose sensor 102. The LIBRE allows calibration-free glucose measurements with an on-skin coin-sized sensor, which can send up to eight hours of data to a reader device (e.g., the device 200) via near field communications, when brought close together. The LIBRE can be worn for fourteen days in all daily life activities. Referring to block 404, in some embodiments, successive measurements in the plurality of autonomous glucose measurements are taken from the subject at an interval rate of 5 minutes or less, 3 minutes or less, or 1 minute or less.

Block 406. Referring to block 406 of FIG. 4A, in addition to the autonomous glucose measurements of the first data set 220, a second data set 228 is obtained from one or more insulin pens 104 used by the subject to apply the standing insulin regimen. The second data set may be in any format, and in fact may be spread across multiple files or data structures, provided that such files or data structures are addressable by the insulin regimen adjustment module 204 or equivalent process. As such, the instant disclosure leverages the recent advances of insulin administration pens, which have become "smart" in the sense that they can remember the timing and the amount of insulin administered in the past. One example of such an insulin pen 104 is the NovoPen 5. Such pens assists patients in logging doses and prevent double dosing. It is contemplated that insulin pens will be able to send and receive insulin medicament dose volume and timing, thus allowing the integration of continuous glucose monitors 102, insulin pens 104 and the algorithms of the present disclosure. As such, the second data set comprises a plurality of insulin medicament records from one or more insulin pens 104. In some embodiments, these data sets are wireless communicated to the device 200 from the one or more insulin pens 104.

Each insulin medicament record 230 in the plurality of medicament records comprises: (i) a respective insulin medicament injection event 232 including an amount of insulin medicament injected 234 into the subject using a respective insulin pen in the one or more insulin pens and (ii) a corresponding electronic timestamp 238 that is automatically generated by the respective insulin pen 104 upon occurrence of the respective insulin medicament injection event. In some embodiments, additional data is found in the insulin medicament records, such as drug lot number.

Referring to block 408, in some embodiments the device 200 further comprises a wireless receiver (284). In such embodiments, the first data set is obtained wirelessly from a glucose sensor (102) affixed to the subject and/or the second data set is obtained wirelessly from the one or more insulin pens using the wireless receiver.

Referring to block 410, the method continues by identifying a plurality of fasting events using the plurality of autonomous glucose measurements of the subject and the respective timestamps in the first data set. Glucose measurements during fasting events are of importance for measuring basal glucose levels. Such basal glucose levels provide insight on whether the basal insulin medicament dosage in a basal insulin medicament dosage regimen is appropriate. Glucose measurements temporally outside of fasting events are more difficult to interpret because they are confounded by the ingestion of meals, which affects glucose levels.

There are a number of methods for detecting a fasting event using autonomous glucose measurements from a glucose monitor 102. For instance, referring to block 412, in some embodiments a first fasting event (in the plurality of fasting events) is identified in a first time period (e.g., a period of 24 hours) encompassed by the plurality of autonomous glucose measurements by first computing a moving period of variance $\sigma_k^2$ across the plurality of autonomous glucose measurements, where:

$$\sigma_k^2 = \left(\frac{1}{M}\sum_{i=k-M}^{k}(G_i - \bar{G})\right)^2$$

and where, $G_i$ is the $i^{th}$ glucose measurement in the portion k of the plurality of glucose measurements, M is a number of glucose measurements in the plurality of glucose measurements and represents a contiguous predetermined time span, $\bar{G}$ is the mean of the M glucose measurements selected from the plurality of glucose measurements, and k is within the first time period. As an example, the plurality of glucose measurements may span several days or weeks, with autonomous glucose measurements taken every five minutes. A first time period (e.g., one day) k within this overall time span is selected and thus the portion k of the plurality of measurements is examined for a period of minimum variance. The first fasting period is deemed to be the period of minimum variance $$\min_k \sigma_k^2$$

within the first time period. Next, the process is repeated with portion k of the plurality of glucose measurements by examining the next portion k of the plurality of glucose measurements for another period of minimum variance thereby assigning another fasting period. Repetition of this method through all portions k of the plurality of glucose measurements is used to build the plurality of fasting periods.

Block 414. Referring to block 414 of FIG. 46, the method continues by applying a first characterization 244 to each respective fasting event 242 in the plurality of fasting events. FIG. 3 illustrates. For each respective fasting event 242 in the plurality of fasting events there is a first characterization 244 for the respective fasting event. The first characterization 244 is one of basal regimen adherent and basal regimen nonadherent.

A respective fasting event is deemed basal regimen adherent when the second data set includes one or more medicament records that establish, on a temporal and quantitative basis, adherence with the standing basal insulin medicament dosage regimen during the respective fasting event. A respective fasting event is deemed basal regimen nonadherent when the second data set fails to include one or more medicament records that establish, on a temporal and quantitative basis, adherence with the standing basal insulin medicament dosage regimen during the respective fasting event.

Figure 9:
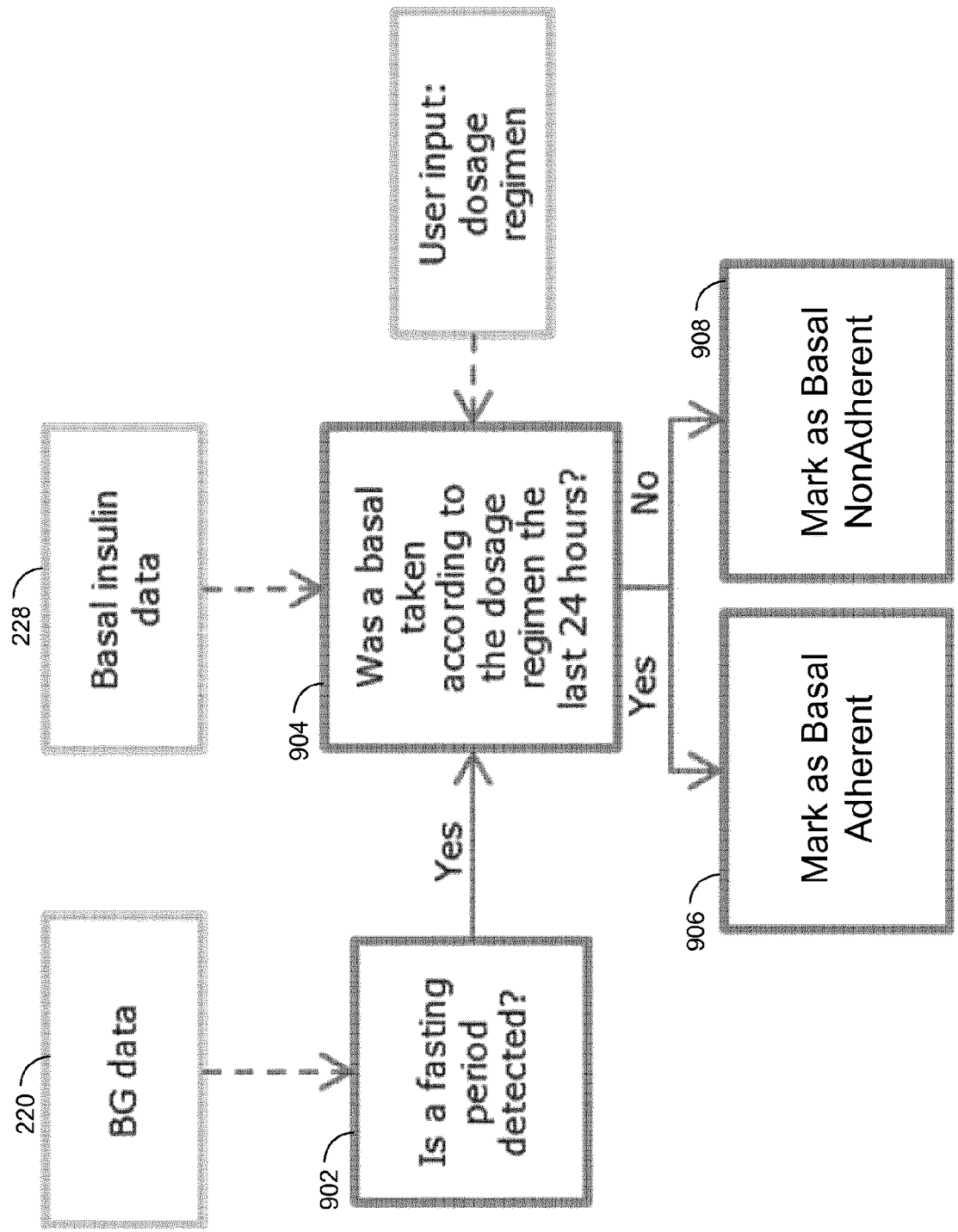
FIG. 9 illustrates an algorithm for calculating basal insulin medicament dosage regimen adherence in which autonomous glucose measurements (BG data) and basal insulin medicament injection events (Basal insulin data) are used as inputs, and where, when a fasting period is detected (e.g. period of minimum variance), the period is classified as "fasting," and where the algorithm checks if a basal injection event has occurred within a period of time specified a standing basal insulin medicament dosage regimen before the fasting event (e.g. basal regimen states one basal injection per day then the algorithm checks if the proper basal insulin medicament was taken during the 24 hours before the detected fasting period) and marks the fasting period as "Basal Adherent" if so, and "Not Basal Adherent" otherwise.
Figure 10:
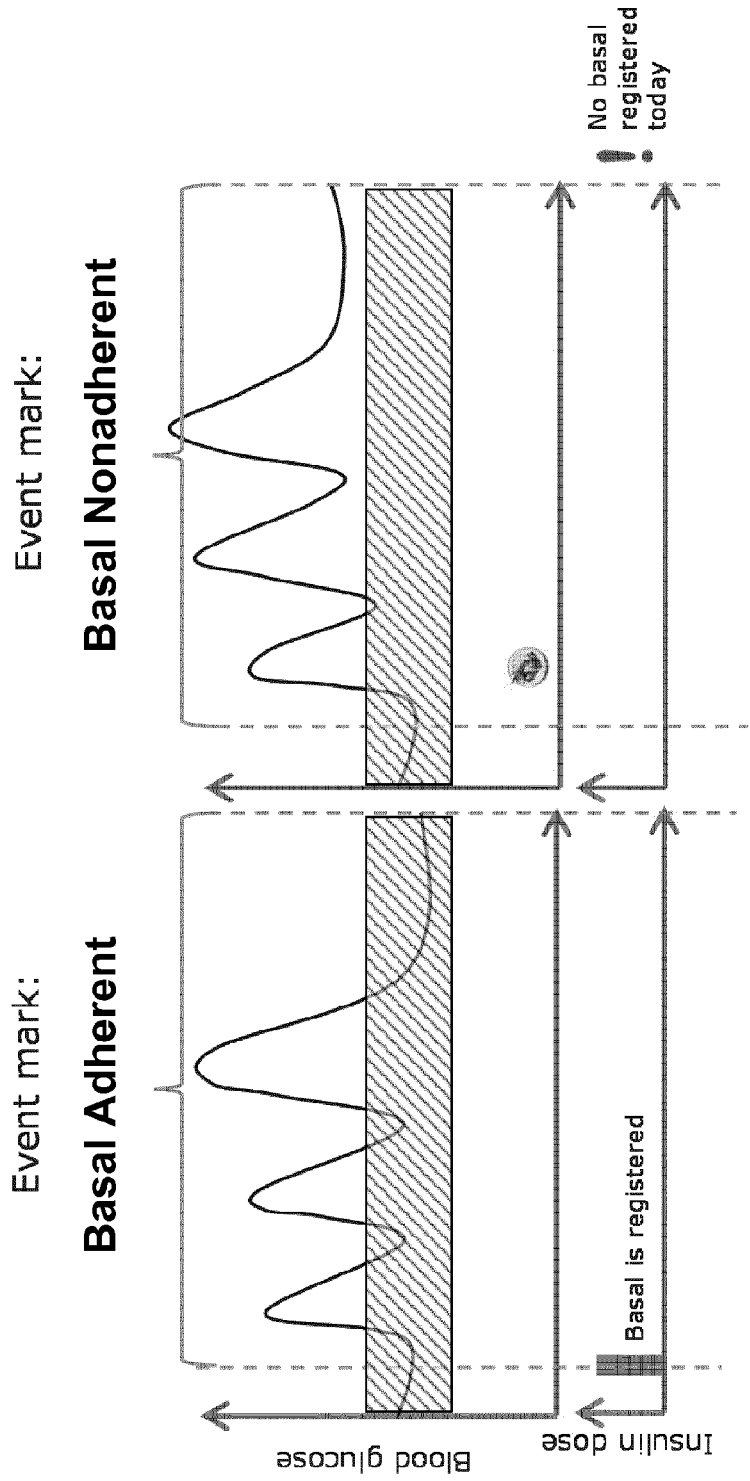
FIG. 10 illustrates an example of basal event marking using the algorithm of FIG. 9 in which basal insulin medicament events are marked as either "Basal Adherent" or "Not Basal Adherent" in accordance with some embodiments.

Referring to block 416, in some embodiments the basal regimen specifies that a basal dose of long acting insulin medicament (210) is to be taken during each respective epoch (212) in a plurality of epochs and that a respective fasting event is deemed basal regimen nonadherent when there are no medicament records in the second data set for the epoch associated with the respective fasting event. In various embodiments, each epoch in the plurality of epochs is two days or less, one day or less, or 12 hours or less (418). Thus, referring to FIG. 9, consider the case where the first data set 220 is used to identify a fasting period 902 and the standing basal insulin medicament dosage regimen specifies to take dosage A of a long acting insulin medicament every 24 hours. In this example, therefore, the epoch is one day (24 hours). The fasting event 242 is inherently timestamped because it is derived from a period of minimum variance in timestamped glucose measurements, or by other forms of analysis of the timestamped autonomous glucose measurements. Thus the timestamp, or period of fasting, represented by a respective fasting event is used as a starting point for examining whether the fasting event is basal regimen adherent 904. For instance, if the period of fasting associated with the respective timestamp is 6:00 AM on Tuesday, May 17, what is sought in the second data set 228 is evidence that the subject took dosage A of the long acting insulin medicament in the 24 hour period (the epoch) leading up to 6:00 AM on Tuesday, May 17 (and not more or less of the prescribed dosage). If the subject took the prescribed dosage of the long acting insulin medicament during this epoch, the respective fasting event (and/or the basal injection event and/or the glucose measurements during this time) is deemed basal regimen adherent 906 (of FIG. 9), and FIG. 10, left panel. If the subject did not take the prescribed dosage of the long acting insulin medicament during this epoch (or took more than the prescribed dosage of the long acting insulin medicament during this period), the respective fasting event (and/or the basal injection event and/or the glucose measurements during this time) is deemed basal regimen nonadherent 908 (of FIG. 9), and FIG. 10, right panel.

Figure 11:
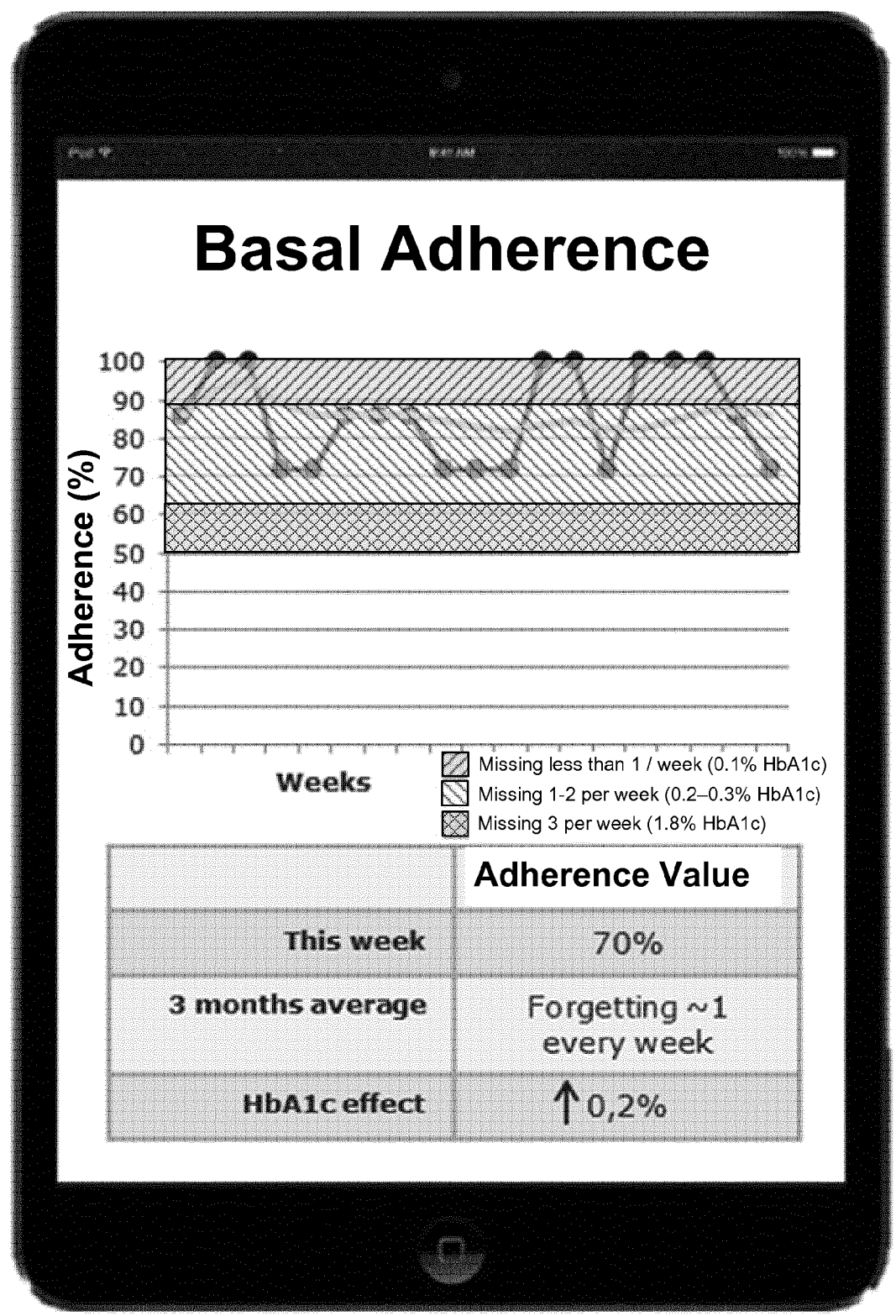
FIG. 11 illustrates an example of basal regimen adherence data interpretation in accordance with an embodiment of the present disclosure.

FIG. 11 illustrates how basal adherence may be plotted as a function of time, showing which basal events are deemed missing, for instance, because certain fasting event were deemed basal regimen nonadherent.

In some embodiments a fasting event is not detected during an epoch when, in fact, the basal insulin medicament regimen specifies that a basal insulin injection event must occur. Thus, the basal injection should be taken according to the prescribed regimen. According to the example above, this epoch would not have a basal adherence categorization for failure to find a fasting event. In some such embodiments, because the basal insulin medicament regimen is known, a determination as to the adherence (of the glucose measurement during the epoch in question and/or the basal injection event in the epoch) based on the basal insulin medicament regimen itself and the injection event data (second data set), and thus does not require detecting the fasting period from the glucose sensor data. As another example, if the basal insulin medicament regimen is once weekly basal injection, the exemplary procedure would look for a basal injection within a seven day window even if a fasting event is not found.

Block 420. Referring to block 420 of FIG. 46, the method continues by adjusting amounts of insulin medicament dosage in the basal insulin medicament dosage regimen for the subject based upon glucose measurements in the first data set that are contemporaneous with the fasting events that are deemed basal regimen adherent and by excluding glucose measurements in the first data set that are contemporaneous with fasting events that are deemed basal regimen nonadherent. Conventional methods for such adjusting may be used, and in fact may be somewhat subjectively based on the health care practitioner's intuition, past experience with a subject, absence or presence of risk factors or other metrics. The innovation here is that data that is used to adjust the insulin medicament dosage in the basal insulin medicament dosage regimen, basal glucose measurements, is obtained without reliance on the subject's manual records. Autonomous glucose records are used to automatically identify fasting events, and only the glucose measurements in the epic associated with fasting event that are deemed basal regimen nonadherent (because the proper basal insulin medicament dosage was taken during the epic) are relied upon to establish basal glucose levels in the subject over time. Glucose measurements in epochs having fasting events that are deemed basal regimen nonadherent are not used.

Referring to block 422 of FIG. 4C, in some embodiments the standing insulin regimen further comprises a bolus insulin medicament dosage regimen 214 in addition to the basal insulin medicament dosage regimen. In some such embodiments, each respective insulin medicament injection event 232 in the plurality of medicament records further indicates a respective type of insulin medicament 236 injected into the subject from one of (i) a long acting insulin medicament and (ii) a short acting insulin medicament. Typically, the long acting insulin medicament is for the basal insulin medicament dosage regimen 208 whereas the short acting insulin medicament is for the bolus insulin medicament dosage regimen 214.

Advantageously, the instant disclosure can also make use of the bolus insulin medicament injection events, when such events are present in the second data set, to provide additional information on the glucose status of the subject. Use of the bolus injection events is particularly helpful because they often occur more frequently than then basal injection events, and thus the bolus injection events often can be used to identify hyperglycaemic or hypoglycaemic events more rapidly than analysis of basal glucose data.

Figure 6:
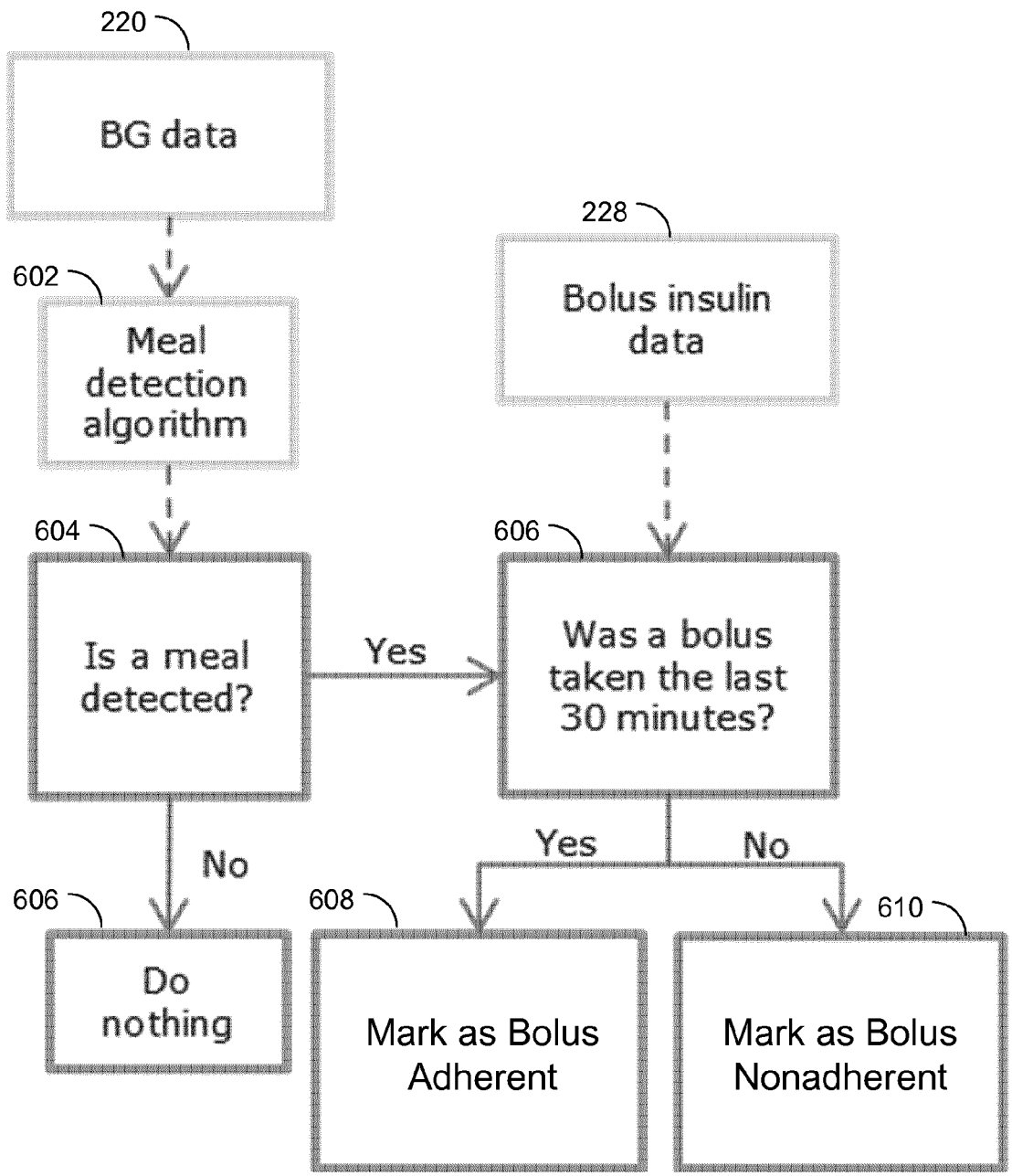
FIG. 6 illustrates an algorithm for calculating bolus insulin medicament regimen adherence, in which autonomous glucose measurements (BG data) and bolus insulin medicament injection event (Bolus insulin data) are inputs, and a meal detection algorithm is used to analyze the autonomous glucose measurements and determine whether a meal was detected or not, in accordance with an embodiment of the present disclosure.

Referring to FIG. 6, in some such embodiments, the bolus insulin medicament injection events in the first data set 220 are made use of in the following way. A plurality of meal events 246 are identified using the plurality of autonomous glucose measurements and the corresponding timestamps in the first data set using a meal detection algorithm (602-604). If no meal is detected, the process ends. If a meal is detected then a second characterization 250 is applied to each respective meal event 248 in the plurality of meal events 606. FIG. 3 illustrates the data structure. The plurality of meal events 246 includes a second characterization 250 for each respective meal event 248. The second characterization is one of bolus regimen adherent and bolus regimen nonadherent.

Referring back to FIG. 6, a respective meal is deemed bolus regimen adherent when one or more medicament records in the plurality of medicament records in the second data set 228 indicates, on a temporal basis, a quantitative basis and a type of insulin medicament basis, adherence with the standing bolus insulin medicament dosage regimen during the respective meal 608. A respective meal is deemed bolus regimen nonadherent when the plurality of medicament records fails to indicate adherence, on a temporal basis, a quantitative basis, and a type of insulin medicament basis, with the standing bolus insulin medicament dosage regimen during the respective meal 608.

Figure 7:
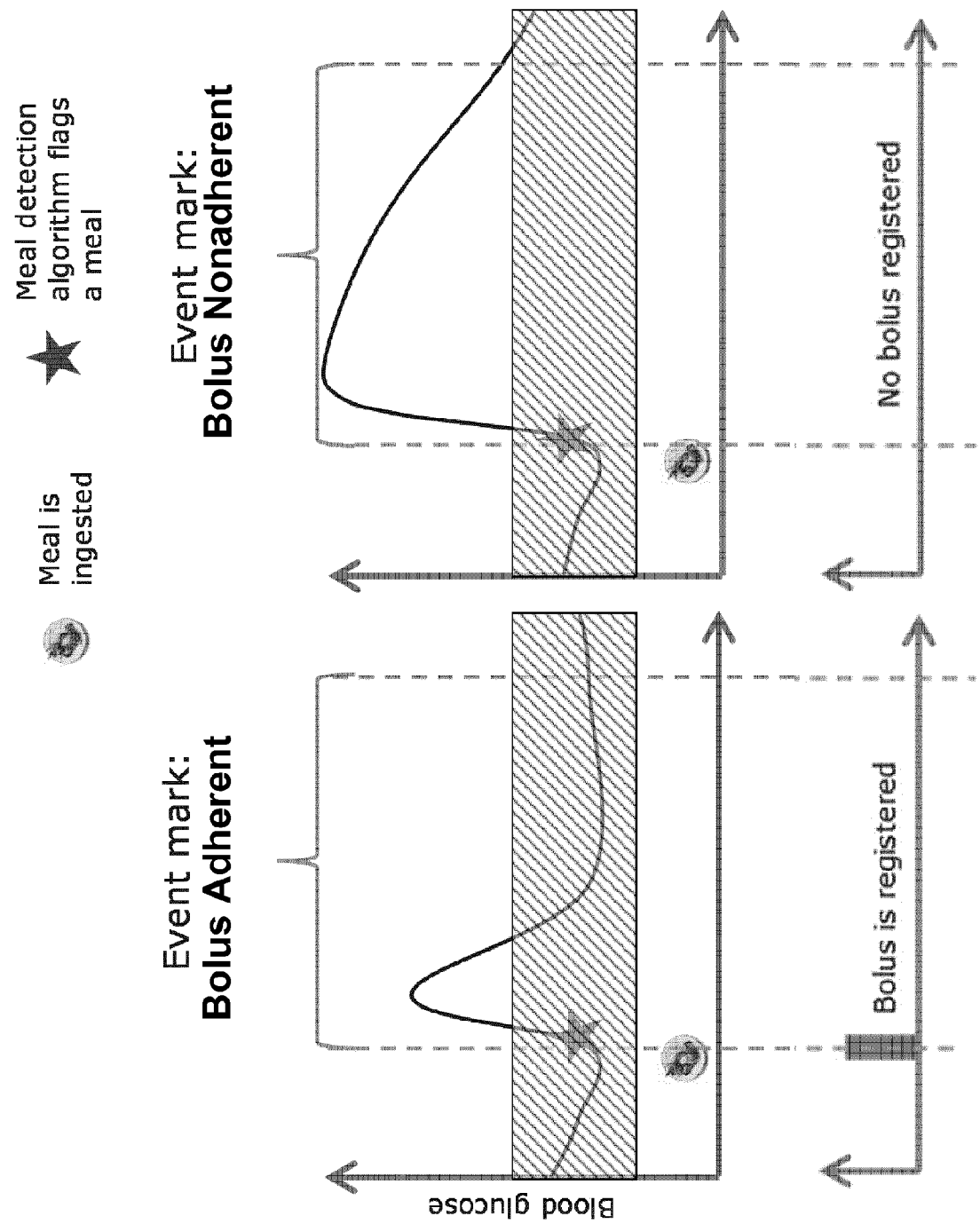
FIG. 7 illustrates an example of a disclosed bolus event marking algorithm, in which insulin medicament injection events are marked as either "Adherent" or "Not Adherent," in accordance with an embodiment of the present disclosure.
Figure 8:
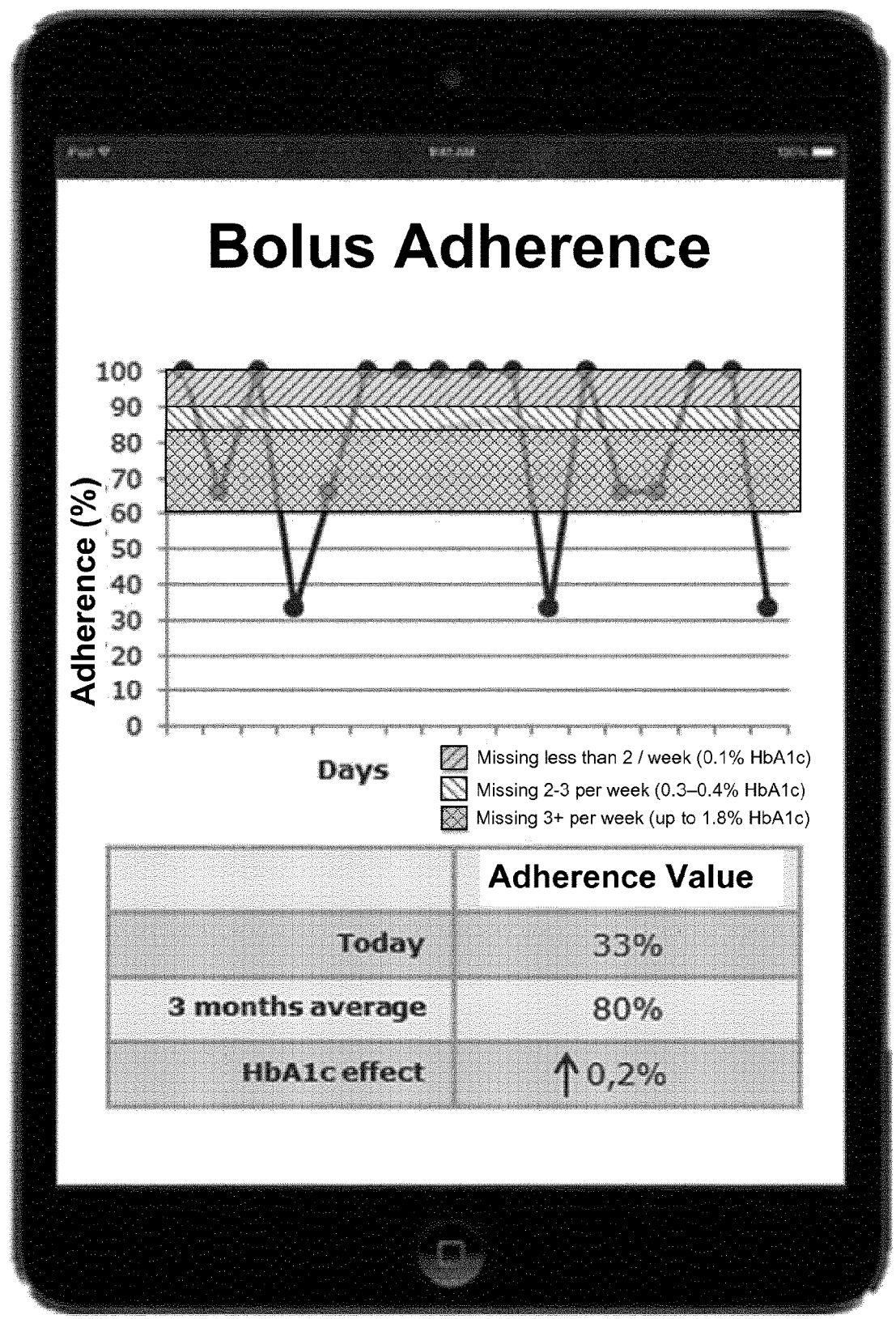
FIG. 8 discloses an example of bolus adherence data interpretation in accordance with an embodiment of the present disclosure.

For instance, consider the case where the standing bolus insulin medicament dosage regimen specifies that dosage A of insulin medicament B is to be taken up 30 minutes before a respective meal and that a certain meal that occurred at 7:00 AM on Tuesday, May 17. It will be appreciated that dosage A may be a function of the anticipated size or type of meal. What is sought in the second data set 228 is evidence that the subject took dosage A of insulin medicament B in the 30 minutes leading up to 7:00 AM on Tuesday, May 17 (and not more or less of the prescribed dosage). If the subject took the prescribed dosage A of the insulin medicament B during the 30 minutes leading up to the respective meal, the respective meal (and/or the bolus administration(s) and/or the glucose measurements during this time) is deemed bolus regimen adherent 608 (of FIG. 6) and FIG. 7 left panel. If the subject did not take the prescribed dosage A of the insulin medicament B during the 30 minutes leading up to the respective meal (or took more than the prescribed dosage A of the insulin medicament B during this period), the respective meal (and/or the bolus administration and/or the glucose measurements during this time) is deemed bolus regimen nonadherent 610 (of FIG. 6) and FIG. 7 right panel. The time period of 30 minutes here is exemplary, in other embodiments the time is shorter or longer (e.g., between 15 minutes to 2 hours prior to the meal and/or is dependent upon the type of insulin medicament prescribed). In other cases the standing bolus insulin medicament dosage regimen specifies that a dosage of insulin is to be taken in a time period following the meal, e.g., 30 minutes or less, 15 minutes or less, 5 minutes or less. In other cases the standing bolus insulin medicament dosage regimen specifies that a dosage of insulin is to be taken in a first predetermined time period before the meal, (e.g., 30 minutes or less, 15 minutes or less, 5 minutes or less), and/or a second predetermined time period after the meal (e.g., 30 minutes or less, 15 minutes or less, 5 minutes or less), where the first predetermined time period is the same or different than the second predetermined time period. FIG. 8 illustrates how bolus adherence may be plotted as a function of time, showing which bolus events are deemed missing, for instance, because certain meals were deemed bolus regimen nonadherent.

In some embodiments, no bolus for a particular meal is required by the bolus insulin medicament dosage regimen and thus that meal is adherent even though there was no bolus prior to the meal. For instance, some bolus regimens only assume a bolus for dinner and not for breakfast and lunch. Therefore a detected lunch meal event but no corresponding bolus would be classified as in adherence.

Further, insulin medicament dosage in the bolus insulin medicament dosage regimen for the subject is adjusted by using glucose measurements in the first data set that are temporally associated with meal events that are deemed bolus adherent and by excluding glucose measurements in the first data set that are temporally associated with meal events that are deemed bolus nonadherent. Conventional methods for such adjusting may be used, and in fact may be somewhat subjectively based on the health care practitioner's intuition, past experience with a subject, absence or presence of risk factors or other metrics. The innovation here is that data that is used to adjust the insulin medicament dosage in the bolus insulin medicament dosage regimen, glucose measurements that are temporally associated with meal events that are deemed bolus adherent, is obtained without reliance on the subject's manual records. Autonomous glucose records are used to automatically identify meal events, and only the glucose measurements that are temporally associated with meal events that are deemed bolus adherent (because the proper bolus insulin medicament dosage was taken prior to meal) are relied upon to establish bolus glucose levels in the subject. Glucose measurements associated with meals that are deemed bolus nonadherent are not used. Moreover, FIG. 8 illustrates how the bolus regimen adherence data can be quantified and visualized.

Referring to block 424, in some embodiments the first data set further comprises a plurality of feed-forward events. In some embodiments, each respective feed-forward event 226 in the plurality of feed-forward events represents an instance where the subject has indicated they are having or are about to have a meal. In such embodiments, the plurality of meal events are verified against the plurality of feed-forward events deduced by way of block 422 by either removing any respective meal event in the plurality of meal events that fails to temporally match any feed-forward event in the plurality of feed-forward events. In other embodiments, feed-forward events are caloric burn rate of the subject, walking events of the subject, exercise events of the subject, and/or sleep events of the subject, some of which may be detected using the optoinal GPS 319, accelerometers 317 or magnetometers of the device 200.

Referring to block 426 of FIG. 4D, in some embodiments, the bolus insulin medicament dosage regimen specifies that the short acting insulin medicament is to be taken up to a predetermined amount of time prior to or after a meal. A respective meal is deemed bolus regimen nonadherent when there is no insulin medicament record of the short acting insulin medicament type having an electronic timestamp up to the predetermined amount of time prior to or after the respective meal. In some such embodiments, the predetermined amount of time is thirty minutes or less, twenty minutes or less, or fifteen minutes or less (428).

Referring to block 430 of FIG. 4D, in some embodiments, the long acting insulin medicament consists of a single insulin medicament having a duration of action that is between 12 and 24 hours or a mixture of insulin medicaments that collectively have a duration of action that is between 12 and 24 hours. Examples of such long acting insulin medicaments include, but are not limited to Insulin Degludec (developed by Novo Nordisk under the brand name Tresiba), NPH (Schmid, 2007, "New options in insulin therapy. J Pediatria (Rio J). 83(Suppl 5):S146-S155), Glargine (LANTUS, Mar. 2, 2007, insulin glargine [rDNA origin] injection, [prescribing information], Bridgewater, N.J.: Sanofi-Aventis), and Determir (Plank et al., 2005, "A double-blind, randomized, dose-response study investigating the pharmacodynamic and pharmacokinetic properties of the long-acting insulin analog detemir," Diabetes Care 28:1107-1112). The short acting insulin medicament consists of a single insulin medicament having a duration of action that is between three to eight hours or a mixture of insulin medicaments that collectively have a duration of action that is between three to eight hours. Examples of such short acting insulin medicaments include, but are not limited, to Lispro (HUMALOG, May 18, 2001, insulin lispro [rDNA origin] injection, [prescribing information], Indianapolis, Ind.: Eli Lilly and Company), Aspart (NOVOLOG, July 2011, insulin aspart [rDNA origin] injection, [prescribing information], Princeton, N.J., Novo Nordisk Inc., July, 2011), Glulisine (Helms Kelley, 2009, "Insulin glulisine: an evaluation of its pharmacodynamic properties and clinical application," Ann Pharmacother 43:658-668), and Regular (Gerich, 2002, "Novel insulins: expanding options in diabetes management," Am J Med. 113:308-316).

Referring to block 432 of FIG. 4D, in some embodiments, the identification of the plurality of meal events is performed by computing: (i) a first model comprising a backward difference estimate of glucose rate of change using the plurality of autonomous glucose measurements, (ii) a second model comprising a backward difference estimate of glucose rate of change based on Kalman filtered estimates of glucose using the plurality of autonomous glucose measurements, (iii) a third model comprising a Kalman filtered estimate of glucose and Kalman filtered estimate of rate of change (ROC) of glucose based on the plurality of autonomous glucose measurements, and/or (iv) a fourth model comprising a Kalman filtered estimate of rate of change of ROC of glucose based on the plurality of autonomous glucose measurements. In some such embodiments, the first model, the second model, the third model and the fourth model are each computed across the plurality of autonomous glucose measurements and each respective meal event in the plurality of meal events is identified at an instance where at least three of the four models indicate a meal event (434). For further disclosure on such meal event detection, see Dassau et al., 2008, "Detection of a Meal Using Continuous Glucose Monitoring," Diabetes Care 31, pp. 295-300, which is hereby incorporated by reference. See also, Cameron et al., 2009, "Probabilistic Evolving Meal Detection and Estimation of Meal Total Glucose Appearance," Journal of Diabetes Science and Technology 3(5), pp. 1022-1030, which is hereby incorporated by reference.

Figure 12:
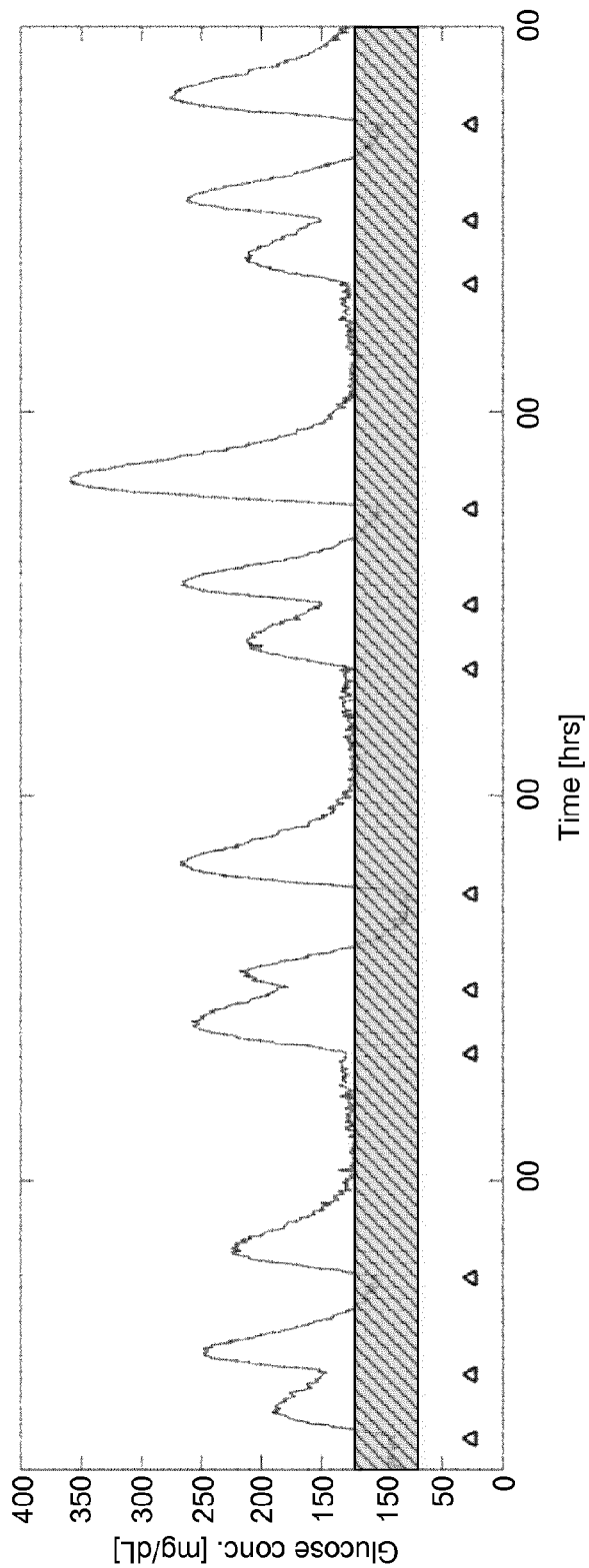
FIG. 12 illustrates the simulation of autonomous glucose data where no knowledge on insulin injection data is available.
Figure 13:
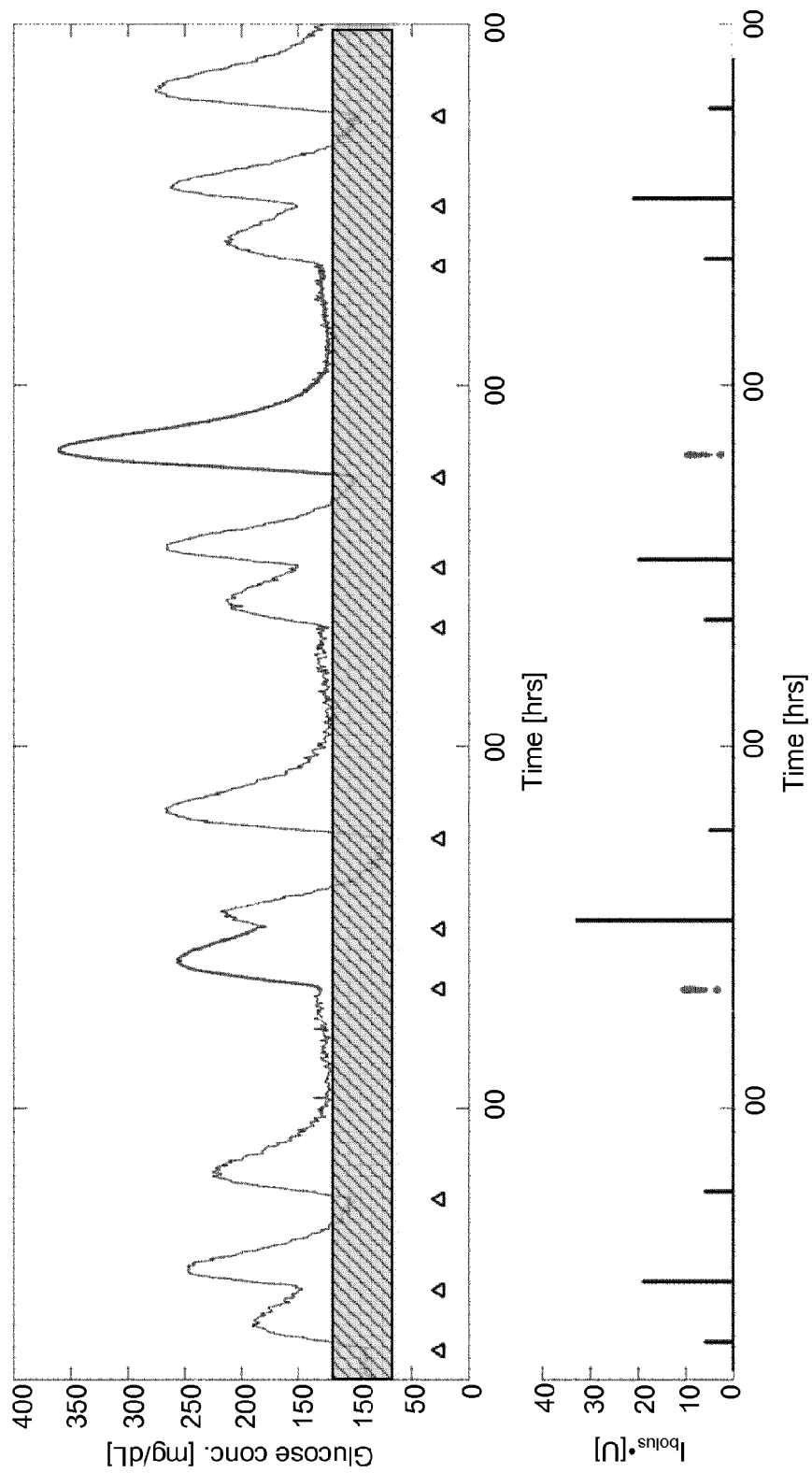
FIG. 13 illustrates the simulation of autonomous glucose data and bolus insulin medicament injections where insulin injection data is available and periods of regimen nonadherence with respect to bolus injection are marked in accordance with some embodiments.

Block 436. Referring to block 436 of FIG. 4D, in some embodiments the method illustrated in FIGS. 4A through 4D is repeated on an ongoing basis over time. In this way, it is possible to adjust the standing insulin regimen 206 for a subject on an ongoing basis. Thus, FIG. 12 illustrates the simulation of autonomous glucose data where no knowledge on insulin injection data is available. By contrast, FIG. 13 illustrates the simulation of autonomous glucose data and bolus insulin medicament injections where insulin injection data is available and periods of nonadherence with respect to a bolus injection are marked in accordance with some embodiments. In this way, it can be seen that spikes in glucose level are related to regimen nonadherence, rather than failure of the dosing regimen to stabilize glucose levels in the subject.

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that comprises a computer program mechanism embedded in a nontransitory computer readable storage medium. For instance, the computer program product could contain the program modules shown in any combination of FIG. 1, 2, or 3 and/or described in FIG. 4. These program modules can be stored on a CD-ROM, DVD, magnetic disk storage product, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

The invention claimed is:

1. A device for adjusting a standing insulin regimen for a subject, the standing insulin regimen comprising a basal insulin medicament dosage regimen, wherein the device comprises one or more processors and a memory, the memory storing instructions that, when executed by the one or more processors, perform a method of:
obtaining a first data set, the first data set comprising a plurality of autonomous glucose measurements of the subject and, for each respective autonomous glucose measurement in the plurality of autonomous glucose measurements, a timestamp representing when the respective measurement was made;
obtaining a second data set from one or more insulin pens used by the subject to apply the standing insulin regimen, the second data set comprising a plurality of insulin medicament records, each insulin medicament record in the plurality of medicament records comprising:
(i) a respective insulin medicament injection event including an amount of insulin medicament injected into the subject using a respective insulin pen in the one or more insulin pens, and
(ii) a corresponding electronic timestamp that is automatically generated by the respective insulin pen upon occurrence of the respective insulin medicament injection event;
identifying a plurality of fasting events using the plurality of autonomous glucose measurements of the subject and the respective timestamps in the first data set;
applying a first characterization to each respective fasting event in the plurality of fasting events, wherein
the first characterization is one of basal regimen adherent and basal regimen nonadherent,
a respective fasting event is deemed basal regimen adherent when the second data set includes one or more medicament records that establish, on a temporal and quantitative basis, adherence with the standing basal insulin medicament dosage regimen during the respective fasting event, and
a respective fasting event is deemed basal regimen nonadherent when the second data set fails to include one or more medicament records that establish, on a temporal and quantitative basis, adherence with the standing basal insulin medicament dosage regimen during the respective fasting event; and
adjusting amounts of insulin medicament dosage in the basal insulin medicament dosage regimen for the subject based upon analysis of glucose measurements in the first data set that are contemporaneous with the fasting events that are deemed basal regimen adherent, wherein such analysis completely excludes all glucose measurements in the first data set that are contemporaneous with fasting events that have been deemed basal regimen nonadherent based on the second data set failing to include the one or more medicament records that establish adherence with the standing basal insulin medicament dosage regimen.

2. The device of claim 1, wherein
the standing insulin regimen further comprises a bolus insulin medicament dosage regimen,
each respective insulin medicament injection event in the plurality of medicament records further indicates a respective type of insulin medicament injected into the subject from one of (i) a long acting insulin medicament and (ii) a short acting insulin medicament, and
the method further comprises:
identifying a plurality of meal events using the plurality of autonomous glucose measurements and the corresponding timestamps in the first data set;
applying a second characterization to each respective meal event in the plurality of meal events, wherein
the second characterization is one of bolus regimen adherent and bolus regimen nonadherent,
a respective meal is deemed bolus regimen adherent when one or more medicament records in the plurality of medicament records indicates, on a temporal basis, a quantitative basis and a type of insulin medicament basis, adherence with the standing bolus insulin medicament dosage regimen during the respective meal, and
a respective meal is deemed bolus regimen nonadherent when the plurality of medicament records fails to indicate adherence, on a temporal basis, a quantitative basis, and a type of insulin medicament basis, with the standing bolus insulin medicament dosage regimen during the respective meal; and
adjusting insulin medicament dosage in the standing insulin medicament regimen for the subject by using glucose measurements in the first data set that are temporally associated with meal events that are deemed bolus regimen adherent and by excluding glucose measurements in the first data set that are temporally associated with meal events that are deemed bolus regimen nonadherent.

3. The device of claim 1, the device further comprising a wireless receiver, and wherein the first data set is obtained wirelessly from a glucose sensor affixed to the subject and/or the second data set is obtained wirelessly from the one or more insulin pens.

4. The device of claim 2, wherein
the first data set further comprises a plurality of feed-forward events,
each respective feed-forward event in the plurality of feed-forward events represents an instance where the subject has indicated they are having or are about to have a meal, and
the plurality of meal events are verified against the plurality of feed-forward events by either removing any respective meal event in the plurality of meal events that fails to temporally match any feed-forward event in the plurality of feed-forward events.

5. The device of claim 1, wherein successive measurements in the plurality of autonomous glucose measurements are taken from the subject at an interval rate of 5 minutes or less, 3 minutes or less, or 1 minute or less.

6. The device of claim 1, wherein the basal regimen is associated with a plurality of epochs, the basal regimen specifies that a basal dose of long acting insulin medicament is to be taken during each respective epoch in the plurality of epochs, and a respective fasting event is deemed basal regimen nonadherent when there are no medicament records in the second data set for the epoch associated with the respective fasting event.

7. The device of claim 6, wherein each epoch in the plurality of epochs is one week or less, two days or less, one day or less, or 12 hours or less.

8. The device of claim 2, wherein
the bolus insulin medicament dosage regimen specifies that the short acting insulin medicament is to be taken up to a predetermined amount of time prior to or after a meal, and
a respective meal is deemed bolus regimen nonadherent when there is no insulin medicament record of the short acting insulin medicament type having an electronic timestamp up to the predetermined amount of time prior to or after the respective meal.

9. The device of claim 8, wherein the predetermined amount of time is thirty minutes or less, twenty minutes or less, or fifteen minutes or less.

10. The device of claim 2, wherein
the long acting insulin medicament consists of a single insulin medicament having a duration of action that is between 12 and 24 hours or a mixture of insulin medicaments that collectively have a duration of action that is between 12 and 24 hours, and
the short acting insulin medicament consists of a single insulin medicament having a duration of action that is between three to eight hours or a mixture of insulin medicaments that collectively have a duration of action that is between three to eight hours.

11. The device of claim 2, wherein the identifying the plurality of meal events is performed by computing:
(i) a first model comprising a backward difference estimate of glucose rate of change using the plurality of autonomous glucose measurements,
(ii) a second model comprising a backward difference estimate of glucose rate of change based on Kalman filtered estimates of glucose using the plurality of autonomous glucose measurements,
(iii) a third model comprising a Kalman filtered estimate of glucose and Kalman filtered estimate of rate of change (ROC) of glucose based on the plurality of autonomous glucose measurements, or
(iv) a fourth model comprising a Kalman filtered estimate of rate of change of ROC of glucose based on the plurality of autonomous glucose measurements.

12. The device of claim 11, wherein the first model, the second model, the third model and the fourth model are each computed across the plurality of autonomous glucose measurements and each respective meal event in the plurality of meal events is identified at an instance where at least three of the four models indicates a meal event.

13. The device of claim 1, the method further comprising repeating the method on an ongoing basis over time.

14. The device of claim 1, wherein the identifying the plurality of fasting events comprises identifying a first fasting period in a first time period encompassed by the plurality of autonomous glucose measurements by:
computing a moving period of variance $\sigma_k^2$ across the plurality of autonomous glucose measurements, wherein:

$$\sigma_k^2 = \frac{1}{M} \sum_{i=k-M+1}^{k} (G_i - \overline{G})^2$$

wherein,
$G_i$ is the $i^{th}$ autonomous glucose measurement in a portion k of the plurality of autonomous glucose measurements,
M is a number of autonomous glucose measurements in the plurality of glucose measurements and represents a contiguous predetermined time span,
$\overline{G}$ is the mean of the autonomous glucose measurements selected from the plurality of autonomous glucose measurements, and
k is within the first time period; and
associating the first fasting period with a period of minimum variance $$\min_{k} \sigma_k^2$$

within the first time period.

15. A method for adjusting a standing insulin regimen for a subject, the standing insulin regimen comprising a basal insulin medicament dosage regimen, the method comprising:
obtaining a first data set, the first data set comprising a plurality of autonomous glucose measurements of the subject and, for each respective autonomous glucose measurement in the plurality of autonomous glucose measurements, a timestamp representing when the respective measurement was made;
obtaining a second data set from one or more insulin pens used by the subject to apply the standing insulin regimen, the second data set comprising a plurality of insulin medicament records, each insulin medicament record in the plurality of medicament records comprising: (i) a respective insulin medicament injection event including an amount of insulin medicament injected into the subject using a respective insulin pen in the one or more insulin pens and (ii) a corresponding electronic timestamp that is automatically generated by the respective insulin pen upon occurrence of the respective insulin medicament injection event;
identifying a plurality of fasting events using the plurality of autonomous glucose measurements of the subject and the respective timestamps in the first data set;
applying a first characterization to each respective fasting event in the plurality of fasting events, wherein
the first characterization is one of basal regimen adherent and basal regimen nonadherent,
a respective fasting event is deemed basal regimen adherent when the second data set includes one or more medicament records that establish, on a temporal and quantitative basis, adherence with the standing basal insulin medicament dosage regimen during the respective fasting event, and
a respective fasting event is deemed basal regimen nonadherent when the second data set fails to include one or more medicament records that establish, on a temporal and quantitative basis, adherence with the standing basal insulin medicament dosage regimen during the respective fasting event; and
adjusting amounts of insulin medicament dosage in the basal insulin medicament dosage regimen for the subject based upon analysis of glucose measurements in the first data set that are contemporaneous with the fasting events that are deemed basal regimen adherent, wherein such analysis completely excludes all glucose measurements in the first data set that are contemporaneous with fasting events that have been deemed basal regimen nonadherent based on the second data set failing to include the one or more medicament records that establish adherence with the standing basal insulin medicament dosage regimen.

\* \* \* \* \*